(12) United States Patent
Kim et al.

(10) Patent No.: US 11,779,464 B2
(45) Date of Patent: Oct. 10, 2023

(54) CUSTOMIZED VENTRICULAR SUPPORT DEVICE

(71) Applicant: WAKE FOREST UNIVERSITY HEALTH SCIENCES, Winston-Salem, NC (US)

(72) Inventors: Phillip Kim, Winston-Salem, NC (US); Anthony Atala, Winston-Salem, NC (US); David James Mccoul, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 901 days.

(21) Appl. No.: 16/618,926

(22) PCT Filed: Jun. 12, 2018

(86) PCT No.: PCT/US2018/037059
§ 371 (c)(1),
(2) Date: Dec. 3, 2019

(87) PCT Pub. No.: WO2018/231794
PCT Pub. Date: Dec. 20, 2018

(65) Prior Publication Data
US 2020/0085579 A1   Mar. 19, 2020

Related U.S. Application Data

(60) Provisional application No. 62/518,884, filed on Jun. 13, 2017.

(51) Int. Cl.
| | |
|---|---|
| *A61F 2/24* | (2006.01) |
| *A61B 34/10* | (2016.01) |
| *G16H 50/50* | (2018.01) |
| *G16H 30/40* | (2018.01) |
| *G06F 30/20* | (2020.01) |

(Continued)

(52) U.S. Cl.
CPC ............ *A61F 2/2481* (2013.01); *A61B 34/10* (2016.02); *G06F 30/20* (2020.01); *G16H 30/40* (2018.01);

(Continued)

(58) Field of Classification Search
CPC ... G06F 30/20; G16H 50/50; A61B 2034/102; A61B 2034/105; B33Y 80/00
See application file for complete search history.

(56) References Cited

U.S. PATENT DOCUMENTS

| | | |
|---|---|---|
| 6,572,533 B1 | 6/2003 | Shapland et al. |
| 2008/0133040 A1 | 6/2008 | Boyden et al. |

(Continued)

FOREIGN PATENT DOCUMENTS

| | | | | |
|---|---|---|---|---|
| WO | WO-2013082505 A1 * | 6/2013 | ............ | A61M 1/122 |
| WO | 2015/0153832 | 10/2015 | | |

OTHER PUBLICATIONS

Park, J., & Park, S. I. (2000). Strain analysis and visualization: left ventricle of a heart. Computers & Graphics, 24(5), 701-714. (Year: 2000).*

(Continued)

*Primary Examiner* — Bijan Mapar
(74) *Attorney, Agent, or Firm* — Myers Bigel, P.A.

(57) ABSTRACT

Provided herein is a method of forming a ventricular support device for a diseased heart, including providing imaging data of the diseased heart, forming a three-dimensional (3D) heart model based on the imaging data, providing strain data including a plurality of strain estimates for at least one segment of the diseased heart, mapping the plurality of strain estimates onto corresponding portions of the 3D heart model to form a 3D diseased heart model, based on the 3D diseased heart model, forming a model of the ventricular support device configured to surround at least a portion of the diseased heart and provide support based upon said strain estimates, and converting the model of the ventricular support device to a digital file useful for directing a 3D printer device to print said ventricular support device for said diseased heart. Also provided is a customized ventricular support device so produced.

34 Claims, 22 Drawing Sheets

(51) Int. Cl.
*B33Y 50/02* (2015.01)
*B33Y 80/00* (2015.01)

(52) U.S. Cl.
CPC ........ *G16H 50/50* (2018.01); *A61B 2034/102* (2016.02); *A61B 2034/105* (2016.02); *A61B 2034/108* (2016.02); *A61F 2240/002* (2013.01); *A61F 2250/0097* (2013.01); *B33Y 50/02* (2014.12); *B33Y 80/00* (2014.12)

(56) References Cited

U.S. PATENT DOCUMENTS

2015/0018607 A1 1/2015 Akita et al.
2017/0007403 A1 1/2017 Wildhirt et al.

OTHER PUBLICATIONS

Chung, J. J., Kanade, R., & Atluri, P. (Mar. 2017). New and improved: implications of a cardiac support device composed of biodegradable materials. In Seminars in Thoracic and Cardiovascular Surgery (vol. 29, No. 1, pp. 62-63). Elsevier. (Year: 2017).*

Fukunishi, . . . & Hibino, N. (Apr. 2017). Preclinical study of patient-specific cell-free nanofiber tissue-engineered vascular grafts using 3-dimensional printing in a sheep model. The Journal of thoracic and cardiovascular surgery, 153(4), 924-932. (Year: 2017).*

PCT Notification Concerning Transmittal of International Preliminary Report on Patentability corresponding to International Application No. PCT/US2018/37059, dated Dec. 26, 2019, 12 pages.

International Search Report and Written Opinion corresponding to International Application No. PCT/US2018/37059, dated Aug. 28, 2018, 13 pages.

Rajesh et al. "Nanofibrous patch for cardiac tissue engineering" Abstract 18 pages (2016).

Kirchmajer et al. "An overview of the suitability of hydrogel-forming polymers for extrusion-based 3D-printing" J. Mat. Chem. B, vol. 3, 17 pages (2015).

Chung et al. "Bio-ink properties and printability for extrusion printing living cells" Journal of Biomaterials Science: Polymer Edition, 1(7):763-773 (2013).

* cited by examiner 1110　　　1160　　　1150

1110　　1160

CUSTOMIZED VENTRICULAR SUPPORT DEVICE

RELATED APPLICATIONS

This application is a 35 U.S.C. § 371 national phase application of International Application Serial No. PCT/US2018/037059, filed Jun. 12, 2018, which claims the benefit of U.S. Provisional Patent Application Ser. No. 62/518,884, filed Jun. 13, 2017, the disclosure of which is incorporated herein by reference in its entirety.

BACKGROUND

Ventricular support devices, also known as ventricular wraps, can be used as a treatment for multiple types of heart disease. For example, cardiomyopathy is a type of heart disease in which the muscle of the heart may become enlarged, thick, and/or rigid. In someone suffering from dilated cardiomyopathy, the heart may become enlarged such that it cannot pump blood efficiently. FIGS. 1 and 2 illustrate a comparison between a normal heart and the heart of someone suffering from dilated cardiomyopathy. As shown in FIG. 2, the heart of someone suffering from dilated cardiomyopathy may alter shape over time as a result of the changes in the heart muscle. As the disease progresses, areas of the heart, such as the left ventricle, may undergo remodeling resulting in increased ventricular volume, thinning of the ventricular wall, and overall changes to the geometry of the heart. Such a dilation of one or more chambers of the heart may lead to long-term physical symptoms or even death.

FIG. 3 illustrates a cycle of progression of cardiac injury with respect to ventricular dilation. As noted in FIG. 3, ventricular dilation can lead to increased stress on the walls of the ventricle. This can result from the change of overall geometry of the ventricle, as well as other changes such as thinning of the ventricle walls. Such an increase in stress on the wall of the ventricle may lead to remodeling of the ventricle as the muscle adjusts to the variations in stress applied to the heart structure. The remodeling, itself, can lead to injury to and/or decrease in performance of the heart's operation. The reduced cardiac functioning itself may lead to further dilation, which feeds into the cycle. Thus, cardiomyopathy may progress as a downward spiral that can result in death of the patient if intervention is not taken.

Ventricular support devices such as a ventricular wrap can enclose the heart in a framework that supports the heart muscle. One such ventricular support device is illustrated in U.S. Pat. No. 7,976,454, entitled "Cardiac harness," filed on Aug. 28, 2006, in the United States Patent Office, the entire contents of which are incorporated herein by reference.

As illustrated in FIG. 3, a ventricular wrap can divert the cycle of progression of cardiomyopathy. For example, a ventricular wrap can support a dilated ventricle, which can lead to reduced wall stress. As a result of the reduction in wall stress, the heart may be stopped from remodeling, which can stop or slow the progression of the disease. In some cases, the additional support may even lead to reversed remodeling in which the heart muscle is able to strengthen and repair itself.

Examples of existing ventricular support devices are the CORCAP device manufactured by Acorn Cardiovascular, Inc., of St. Paul, Minnesota, and the HEARTNET device manufactured by Paracor Medical, Inc. of Sunnyvale, California However, improved ventricular support devices are needed, particularly devices that better fit and support a patient's individual heart.

SUMMARY

The foregoing and other objects and aspects of the embodiments taught herein are explained in greater detail in the drawings herein and the specification set forth below.

A method of forming a ventricular support device for a diseased heart is provided, which method may include one or more of the steps of providing imaging data of the diseased heart, forming a three-dimensional (3D) heart model based on the imaging data, providing strain data, said strain data including a plurality of strain estimates for at least one segment of the diseased heart, mapping the plurality of strain estimates onto corresponding portions of the 3D heart model to form a 3D diseased heart model, based on the 3D diseased heart model, forming a model of the ventricular support device, said ventricular support device configured to surround at least a portion of the diseased heart and provide support based upon said strain estimates, and converting the model of the ventricular support device to a digital file, said digital file useful for directing a 3D printer device to print the ventricular support device for the diseased heart.

In some embodiments, the method may include printing the ventricular support device with the 3D printer device.

In some embodiments, the method may include providing an index structure on the model of the ventricular support device. In some embodiments, the index structure comprises a first color and/or pattern different from a second color and/or pattern of material surrounding the index structure.

A method of treating ventricular remodeling in a heart of a subject in need thereof is provided, which method may include one or more of the steps of providing imaging data (e.g., CT or MRI imaging data), forming a 3D heart model based on the imaging data of the heart, providing strain data including a plurality of strain estimates for at least one segment of the heart, mapping the plurality of strain estimates onto corresponding portions of the 3D heart model to form a 3D diseased heart model, based on the 3D diseased heart model, forming a model of a ventricular support device, said device configured to surround at least a portion of the heart and provide support based upon said strain estimates, converting the model of the ventricular support device to a digital file, said digital file useful for directing a 3D printer device to print said ventricular support device, printing said ventricular support device using said digital file, and administering said ventricular support device to the heart of said subject.

In some embodiments, the ventricular remodeling may be left ventricular remodeling. In some embodiments, the subject may have dilated cardiomyopathy. In some embodiments, the subject may have congested heart failure. In some embodiments, the subject may have suffered from myocardial infarction. In some embodiments, the subject may be a human subject. In some embodiments, the ventricular support device may be biodegradable. In some embodiments, the administering may be carried out by laparoscopic surgery.

A computer system is also provided, which may include a processor and a memory coupled to the processor and including computer readable program code. When executed by the processor, the computer readable program code may cause the processor to perform operations, including one or more of: receiving imaging data of a diseased heart; forming a 3D heart model based on the imaging data; receiving strain data, said strain data including a plurality of strain estimates for at least one segment of the diseased heart; mapping the plurality of strain estimates onto corresponding portions of the 3D heart model to form a 3D diseased heart model; based on the 3D diseased heart model, forming a model of a ventricular support device, said ventricular support device configured to surround at least a portion of the heart and provide support based upon said strain estimates; and converting the model of the ventricular support device to a digital file, said digital file useful for directing a 3D printer device to print said ventricular support device for said diseased heart.

In some embodiments, the computer system may include a 3D printer operatively connected to the processor, and the processor may further perform operations including printing the ventricular support device with the 3D printer using the digital file created by a method taught herein.

In some embodiments, the processor may further perform operations including providing an index structure on the model of the ventricular support device.

Further provided is a computer program product which may include a tangible non-transitory computer readable storage medium including computer readable program code as taught herein embodied in the computer readable storage medium. When executed by at least one processor, the computer readable program code may cause the at least one processor to perform operations including one or more of: receiving imaging data of a diseased heart; forming a 3D heart model based on the imaging data; receiving strain data, said strain data including a plurality of strain estimates for at least one segment of the diseased heart; mapping the plurality of strain estimates onto corresponding portions of the 3D heart model to form a 3D diseased heart model; based on the 3D diseased heart model, forming a model of a ventricular support device, said ventricular support device configured to surround at least a portion of the heart and provide support based upon said strain estimates; and converting the model of the ventricular support device to a digital file, said digital file useful for directing a 3D printer device to print said ventricular support device for said diseased heart.

In some embodiments, the computer readable program code may cause the processor to further perform operations including printing the ventricular support device with a 3D printer connected to the processor using the digital file.

In some embodiments, the computer readable program code may cause the processor to further perform operations including providing an index structure on the model of the ventricular support device.

Also provided is a customized ventricular support device for a diseased heart which may include a mesh structure configured to enclose at least a portion of the diseased heart. A first portion of the mesh structure may be configured to support a first portion of the diseased heart, a second portion of the mesh structure may be configured to support a second portion of the diseased heart, and a first characteristic of the first portion of the mesh structure may be different than a second characteristic of the second portion of the mesh structure responsive to differences between the first and second portions of the diseased heart.

In some embodiments, the customized ventricular support device may include an index structure on the ventricular support device. In some embodiments, the index structure may include a first color and/or pattern different from a second color and/or pattern of material surrounding the index structure.

In some embodiments, the mesh structure may be produced by a 3D printer.

In some embodiments, forming the 3D heart model may include making multiple measurements of dimensions of the diseased heart and using said measurements to form the 3D heart model.

In some embodiments, forming a model of the ventricular support device may include associating a first segment of the 3D diseased heart model with a first mapping between a first strain estimate of the plurality of strain estimates and a first portion of the 3D heart model, associating a second segment of the 3D diseased heart model with a second mapping between a second strain estimate of the plurality of strain estimates and a second portion of the 3D heart model, and providing greater reinforcement to the first segment of the 3D diseased heart model than the second segment of the 3D diseased heart model when it is determined that the first strain estimate is greater than the second strain estimate.

In some embodiments, the printing may be carried out using a biodegradable material to form a ventricular support device that is biodegradable (e.g., poly(L-lactide-co-caprolactone) (PLCL), e.g., with a ratio from 50:50 to 80:20).

In some embodiments, the biodegradable material may include an elastomeric polyester (e.g., polycaprolactone (PCL)), and optionally the elastomeric polyester may be crosslinked (e.g., linearly crosslinked).

In some embodiments, the ventricular support device may include a mesh structure comprising a diamond lattice and/or a Voronoi pattern.

One of skill in the art will appreciate that aspects described with respect to one embodiment may be incorporated in different embodiments although not specifically described relative thereto. That is, all embodiments and/or features of any embodiments can be combined in any way and/or combination.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION

Figure 1:
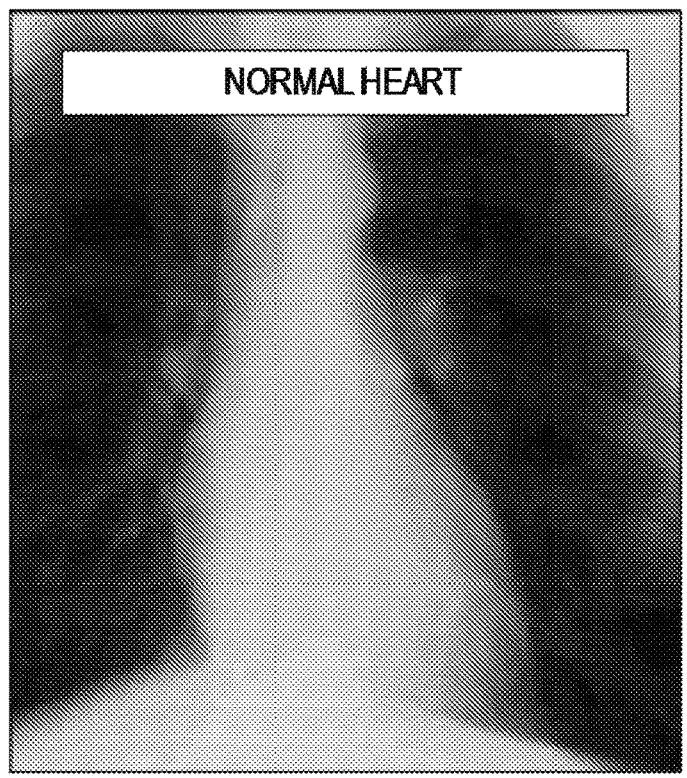
FIG. 1 is an image illustrating a normal heart.
Figure 2:
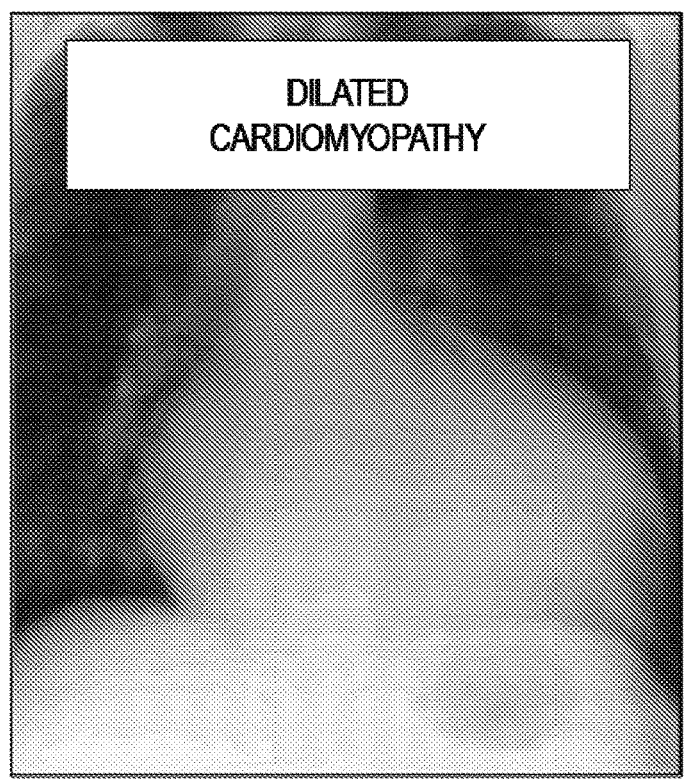
FIG. 2 is an image illustrating a heart of patient suffering from dilated cardiomyopathy.
Figure 3:
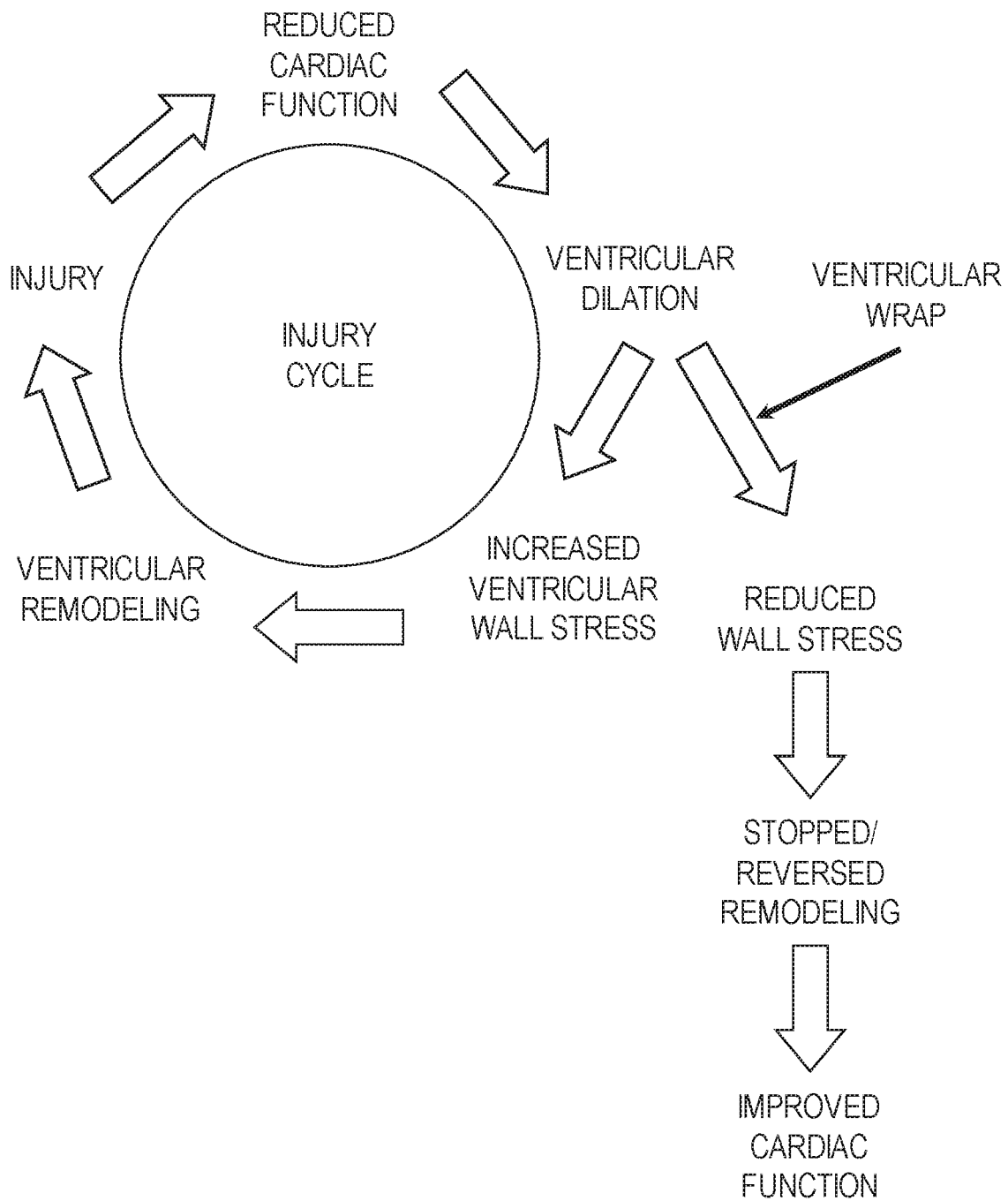
FIG. 3 is a schematic representation of an injury cycle associated with ventricular remodeling, noting possible intervention with a ventricular support device.

Embodiments of the invention are described hereinafter with reference to the accompanying drawings. The present invention may, however, be embodied in different forms and should not be construed as limited to the embodiments set forth herein. Rather, these embodiments are provided so that this disclosure is thorough and complete and fully conveys the scope of the present invention to one skilled in the art.

The terminology used herein is for the purpose of describing particular aspects only and is not intended to be limiting of the embodiments taught herein. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," "on" versus "directly on").

It will be understood that although the terms "first," "second," etc. are used herein to describe members, regions, portions, sections, components, and/or elements in example embodiments taught herein, the members, regions, portions, sections, components, and/or elements should not be limited by these terms. These terms are only used to distinguish one member, region, portion, section, component, or element from another member, region, portion, section, component, or element. Thus, a first member, region, portion, section, component, or element described below may also be referred to as a second member, region, portion, section, component, or element without departing from the scope of the embodiments taught herein. For example, a first element may also be referred to as a second element, and similarly, a second element may also be referred to as a first element, without departing from the scope of the embodiments taught herein.

Like numbers refer to like elements throughout. Thus, the same or similar numbers may be described with reference to other drawings even if they are neither mentioned nor described in the corresponding drawing. Also, elements that are not denoted by reference numbers may be described with reference to other drawings.

As used herein, a "ventricular support device" encompasses devices which can support the structure of the heart by contacting and/or surrounding at least a portion of the lower chambers of the heart. Though specified as a "ventricular" support device, it will be understood that such devices can contact and/or encompass other portions of the heart beyond the ventricles. Ventricular support devices, ventricular wraps, cardiac support devices, and cardiac wraps are considered as synonymous terms for the purposes of this specification.

As used herein a "biodegradable" material encompasses materials which can be inserted into the body and dissolve and/or otherwise be absorbed by the body (e.g., within one or two years of their insertion. In some embodiments, biodegradable material may dissolve and/or otherwise be absorbed within six, seven, or eight months after insertion. In some embodiments, biodegradable material may dissolve and/or otherwise be absorbed within one, two or three months after insertion. Depending on the purpose of the wrap, the degradation rate can be adjusted. For instance, if the wrap is for patients with severe congestive heart failure, in some embodiments the wrap is constructed to last at least six months. However, if the wrap is for use as a man-made pericardium, then the wrap does not necessarily have to last for six months. In some embodiments, the degradation rate may be adjusted by varying the number and/or type of chemical crosslinking in the biodegradable material.

"Subjects" are generally human subjects and include, but are not limited to, "patients." The subjects may be male or female and may, be of any race or ethnicity, including, but not limited to, Caucasian, African-American, African, Asian, Hispanic, Indian, etc. The subjects may be of any age, including newborn, neonate, infant, child, adolescent, adult, and geriatric subjects.

Subjects may also include animal subjects or patients, particularly vertebrate animals, e.g., mammalian subjects such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes.

"Treat" refers to any type of treatment that imparts a benefit to a subject, e.g., a patient afflicted with a cardiac disease. Treating includes actions taken and actions refrained from being taken for the purpose of improving the condition of the patient (e.g., ventricle wall support of a diseased hears in a patient in need thereof, the relief of one or more symptoms, etc.). In some embodiments, treating includes reducing ventricular wall stress, reduction of ventricular remodeling, and or improved cardiac function upon insertion of a ventricular support device as taught herein into a subject in need thereof.

In some embodiments, the subject in need thereof has cardiomyopathy. In some embodiments, the subject in need thereof has congested heart failure. In some embodiments, the subject in need thereof has suffered from myocardial infarction.

Existing ventricular support devices are normally configured as a uniform mesh that fully encircles the heart of the patient. Because the mesh provides pressure equally to each of the encompassed portions of the heart, the external pressure applied to the wall of the heart may be too great in some segments of the patient's heart while too little in other segments of the patient's heart. For example, while one portion of the patient's heart may require an application of a particular magnitude of pressure in order to provide a beneficial outcome, that same pressure may result in a negative outcome if uniformly applied to other parts of the heart. As a result of the uniform application, a pressure below that which would be optimal may be applied. Similarly, when a ventricular support device is a uniform size, even if it has expansion capabilities, it results in a greater pressure being applied to a larger heart and a lesser pressure being applied to a smaller heart. In addition, segments of the patient's heart that may require greater care cannot be addressed by a uniform design. This one-size-fits-all model may thus result in suboptimal results for a majority of patients with which it is used.

In addition, existing ventricular support devices are often constructed of materials which do not dissolve in the patient's body. As a result, when the treatment is complete, the device must be removed, which induces greater risk and complexity into the treatment.

Figure 4:
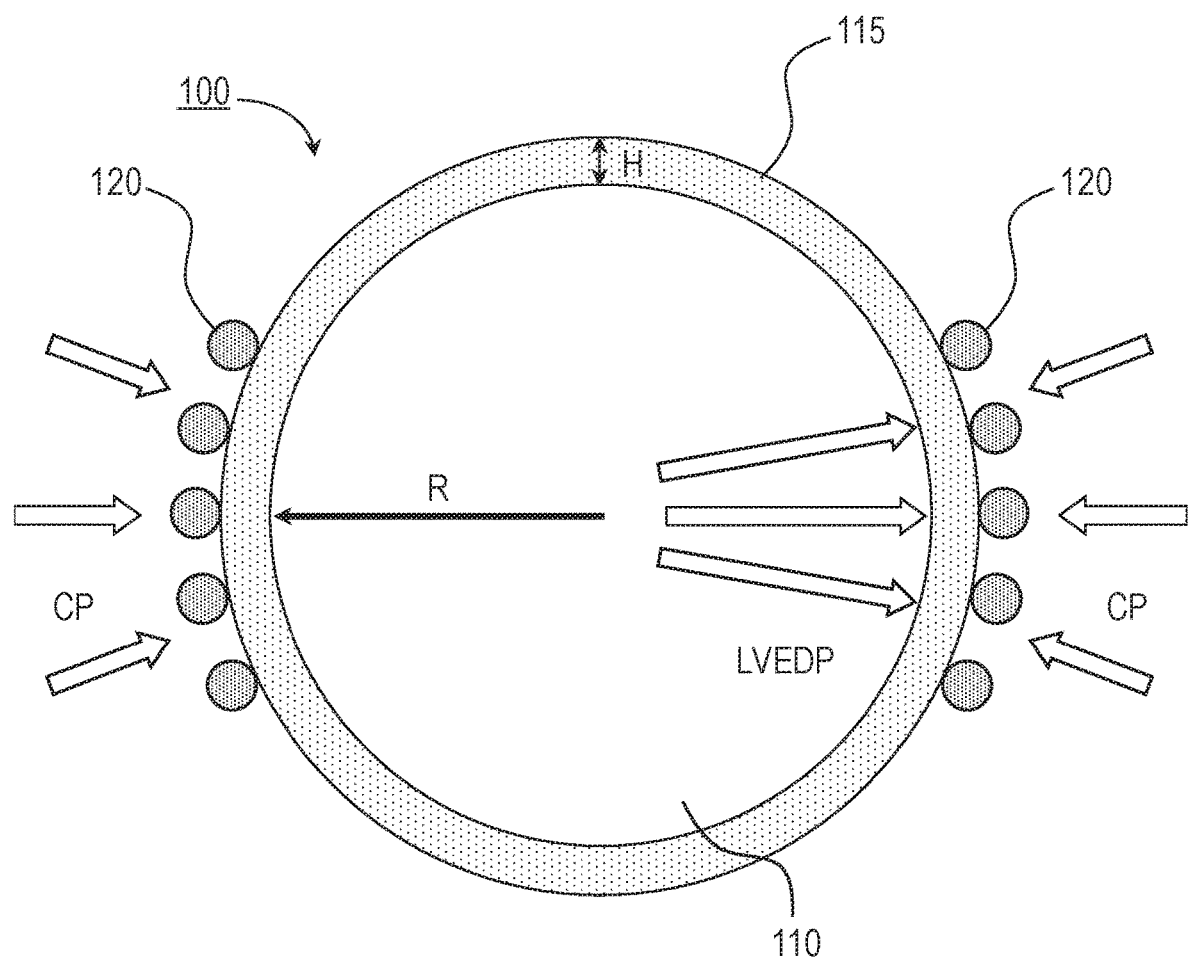
FIG. 4 is a schematic representation of a stress model of a chamber of the heart.

FIG. 4 illustrates a symbolic view of the pressure applied within a cross-section of a chamber 110 of a heart 100. As shown in FIG. 4, the chamber 110 has a radius R. The overall chamber 110 also has a wall 115, with a wall thickness H. The normal operation of the heart may generate a transmural pressure on the wall 115 of the chamber 110. One such measure of the pressure experienced in, for example, the left ventricle is the left ventricular end-diastolic pressure (LVEDP). LVEDP is the pressure at the end of diastole measured in the left ventricle after it has filled up with blood from the left atrium. For a given LVEDP, the stress on the wall 115 of the chamber 110 (e.g. a myocardial or diastolic wall stress) may be given by the equation:

$$\text{Diastolic wall stress} = (R*\text{LVEDP})/H$$

Thus, as can be seen, if the radius of the chamber increases, or the thickness of the wall decreases, the wall stress may increase. A ventricular support device provides a support device 120 with structures that can apply a counterpressure (CP) to the wall 115 of the chamber 110. The support device 120 may take the form of a band or wrap which surrounds the chamber 110. When such a support device 120 is present, the stress on the wall 115 of the chamber 110 may be given by the equation:

$$\text{Diastolic wall stress} = (R*(\text{LVEDP}-\text{CP}))/H$$

As shown in the equation above, the addition of the ventricular support device 120 may provide the counterpressure (CP) to reduce the overall wall stress experienced by the patient's heart.

Figure 5:
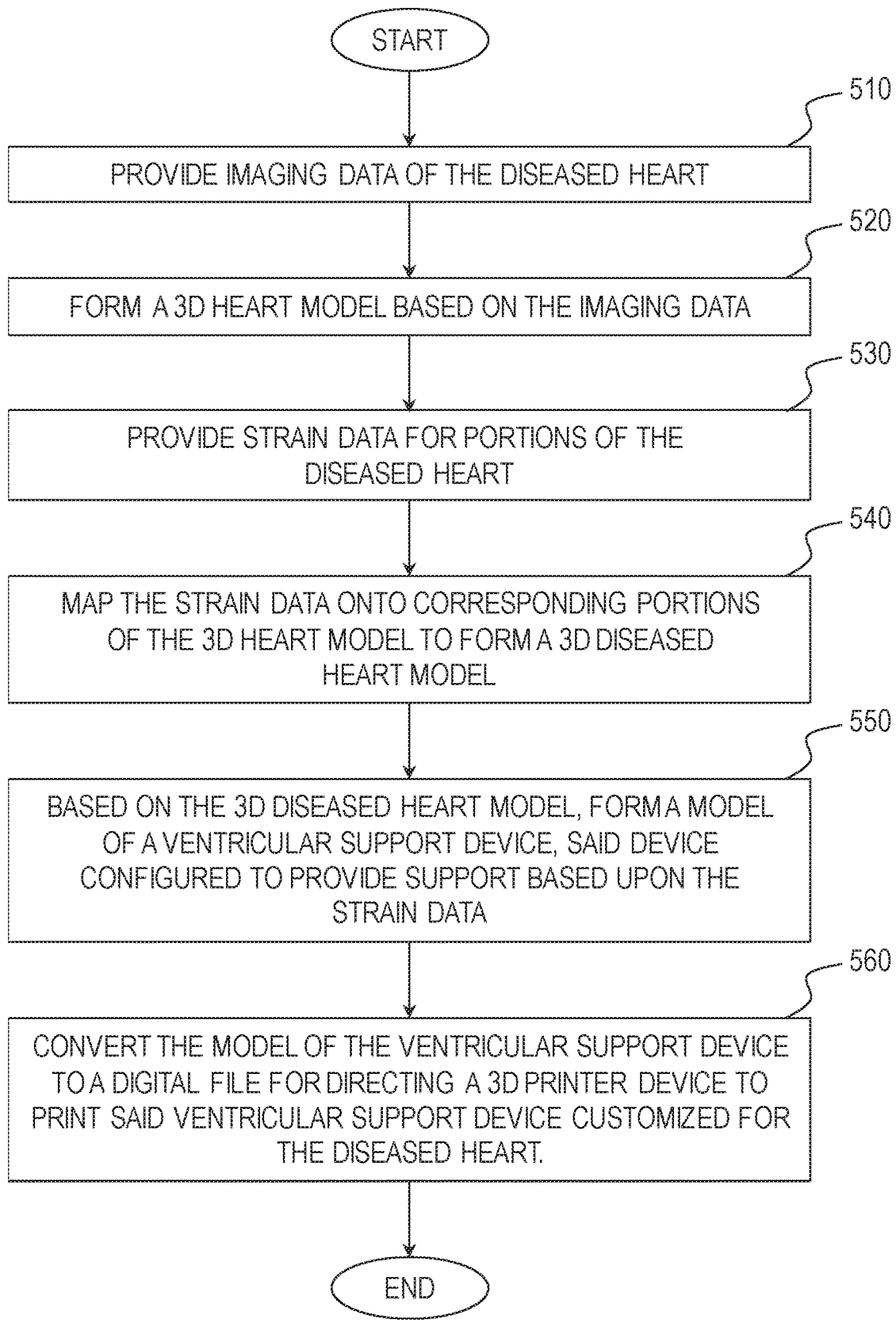
FIG. 5 illustrates a method for generating an improved ventricular support device according to some embodiments taught herein.

FIG. 5 illustrates a method for generating a print file for an improved ventricular support device according to some embodiments of the present invention. The ventricular support device is customized to the support requirements of the patient for which it is designed. Moreover, the ventricular support device of the embodiments taught herein may be rapidly constructed by 3D printing of a biodegradable material which does not require additional procedures for removal when the treatment process is complete.

In some embodiments, the method for generating the ventricular support device begins at operation 510 with the procurement of imaging data of the diseased heart for which the ventricular support device is intended. The imaging data may include magnetic resonance imaging (MRI) data, a computerized axial tomography (CAT) scan, an echocardiography scan, and/or a positron emission tomography (PET) scan, though the embodiments taught herein are not limited thereto. In some embodiments, medical imaging modalities which provide a Digital Imaging and Communications in Medicine (DICOM) image format may be supported, though the embodiments taught herein are not limited to DICOM image formats. The imaging data may provide measurement, contour, and/or other image data showing physical characteristics of the patient's heart.

Figure 6:
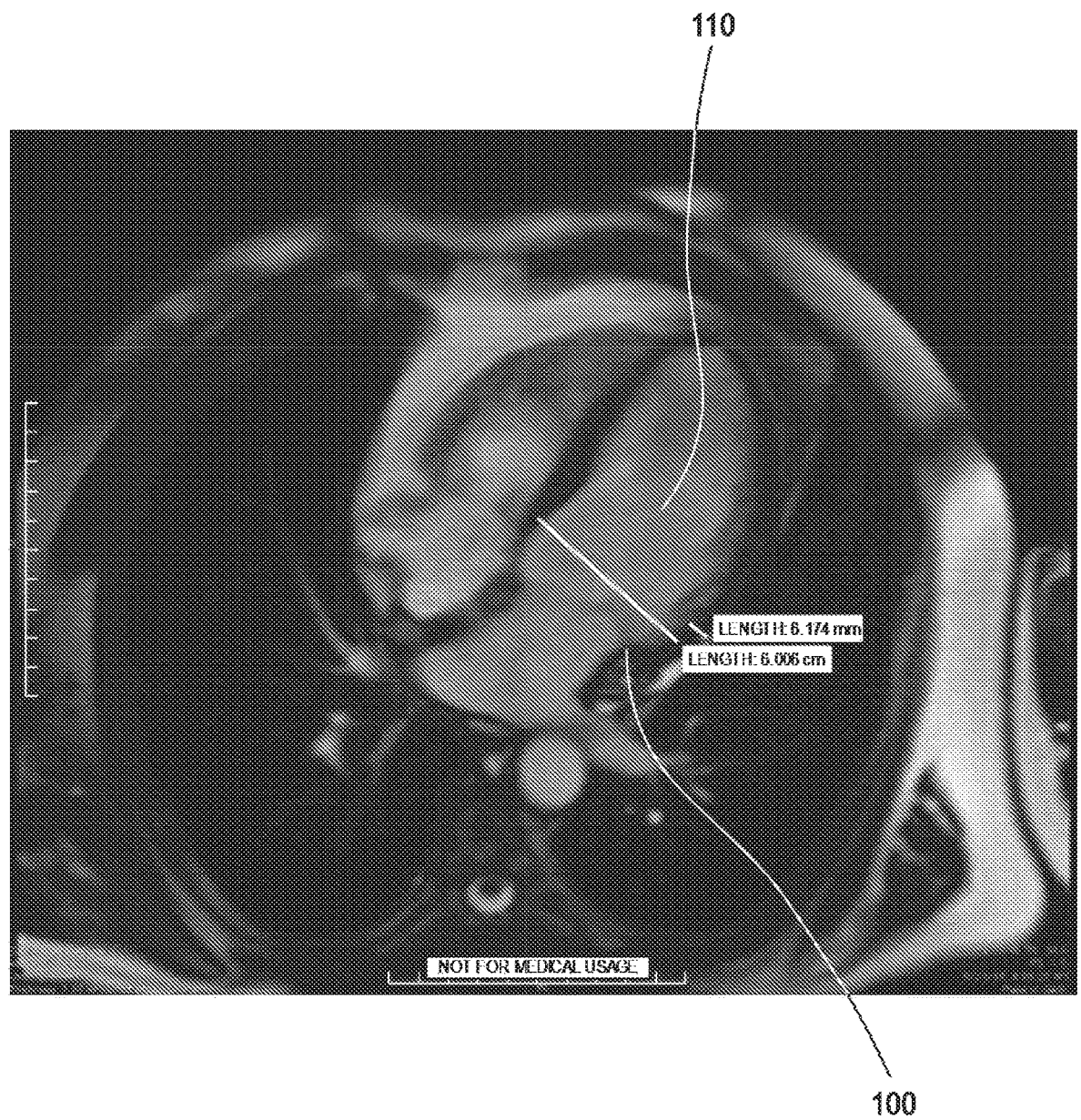
FIG. 6 illustrates an example of imaging data for a diseased heart.

FIG. 6 illustrates an example of imaging data for a diseased heart 100. As illustrated in FIG. 6, an image of the diseased heart 100 may include a scan from which physical characteristics of the diseased heart 100 may be determined. For example, as shown in FIG. 6, the imaging data may be used to determine physical dimensions of the diseased heart 100, such as the outer dimensions of the heart chamber 110.

Referring back to FIG. 5, the method may include operation 520 in which a 3D heart model is formed based on the physical characteristics of the diseased heart 100 obtained from the imaging data. For example, as discussed with respect to FIG. 6, various characteristics such as length, width, shape, volume, etc. may be determined from the imaging data. Based on these characteristics, a 3D model of the heart is generated. In some embodiments, the 3D model may combine data from multiple forms of provided imaging data into a single 3D representation of the heart. Methods of generating a heart model based on imaging data are discussed, for example, in U.S. Pat. No. 7,693,563, entitled "Method for image processing and contour assessment of the heart," the entire contents of which are included by reference herein. As used herein, the "3D model" may include some, but not necessarily all, of the physical characteristics of the diseased heart 100. For example, characteristics of the patient's heart that may be included are myocardial stiffness, ventricle wall thickness, heart rate, ventricle wall tension, right and left ventricle volumes, mitral valve annulus, chordae tendinae, papillary muscles, mitral valve leaflets, ventricle endocardium border, ventricle epicardium border, aortic valve annulus, aortic valve cusps, tricuspid valve apparatus, pulmonary valve apparatus, ventricle wall thickness, ventricle areas of akinesia, ventricle areas of dyskinesia, ventricle areas of asynergy, ventricle preload, ventricle filling pressure, heart's arterial system, heart's flow through the arterial system, heart's venous system, left and right atrium volumes, left and right atrium wall thickness. Similarly, though the model includes characteristics of the heart encompassing three dimensions, the 3D model is not limited to a visual model. The 3D model may include any combination of data which can represent the physical characteristics of the heart in three dimensions.

The method may also include operation 530 in which strain data is provided for portions of the diseased heart. Strain data may include estimates of the strain experienced by the diseased heart 100 at various portions of the diseased heart 100. Because the anatomy of the heart is asymmetrical, different portions of the heart experience different levels of pressure as blood flows through the heart during a cardiac cycle. Strain data may include, among other measurements, a maximum strain level, or pressure, experienced by a given segment of the diseased heart 100 over the cardiac cycle. The strain data may be estimates based on the imaging data and/or other measurements. In some embodiments, the strain data may be based on the volume and/or shape of the diseased heart 100 as determined by the imaging data provided in operation 510.

Figure 7:
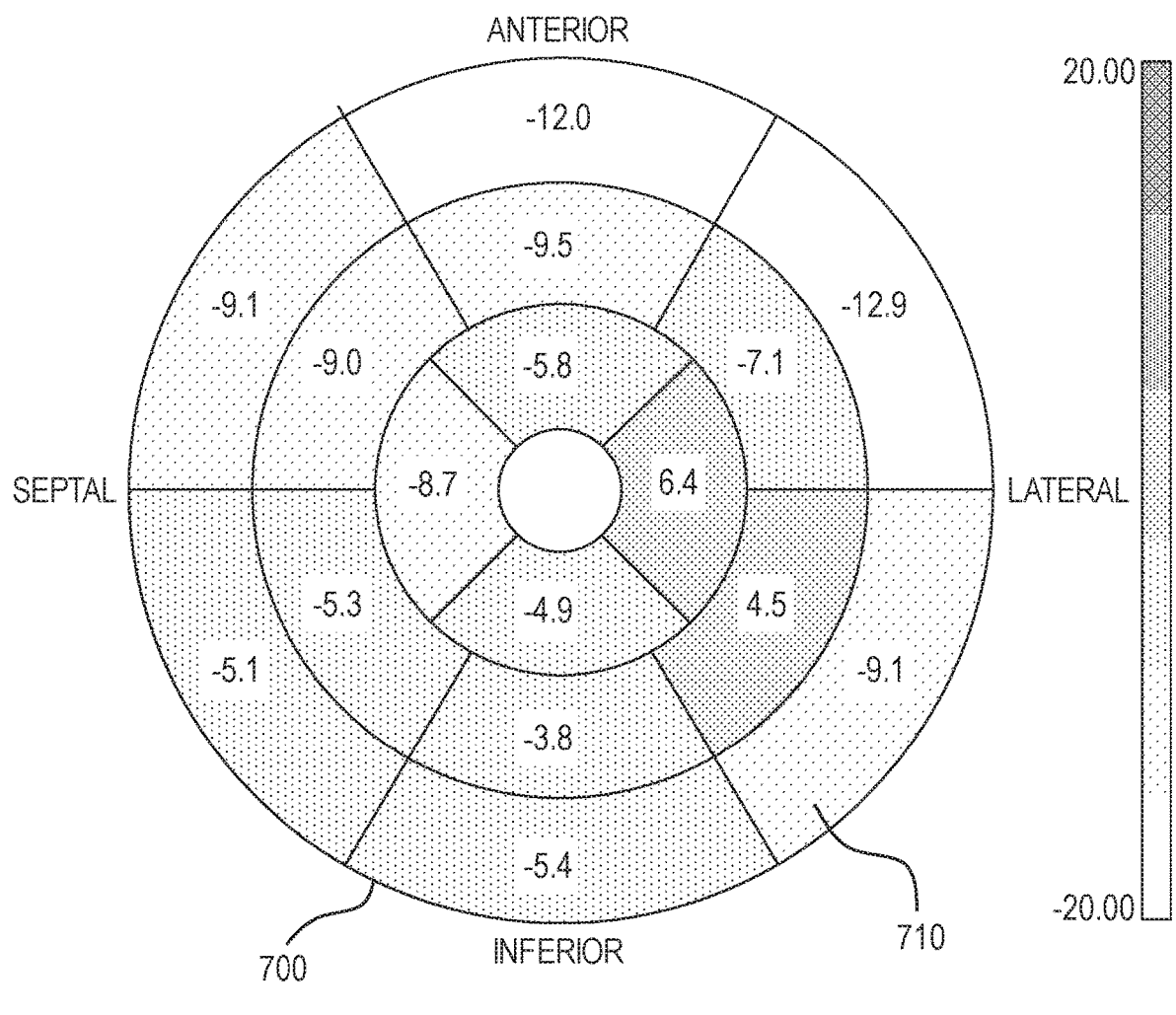
FIG. 7 illustrates an example set of strain estimates for a diseased heart.

FIG. 7 illustrates an example set of strain estimates 700 for a diseased heart 100. As illustrated in FIG. 7, the strain estimates 700 may be broken into individual segments, or portions, 710 of the heart. In particular, the segmentation of FIG. 7 illustrates a mapping for a left ventricle. The mapping may assign strain estimates to particular segments 710 of the wall of the diseased heart based on the location of the segment 710 within the diseased heart. As illustrated, the strain estimates may be different based on their location. FIG. 7 is one example illustrating the strain in a first plane (e.g. anterior, inferior, septal, and/or lateral direction) as well as a second plane (basal, mid-cavity, and apical direction). Though FIG. 7 illustrates one example of strain data, the embodiments taught herein are not limited thereto. In some embodiments, the strain data may be numerical values associated with a plurality of segments of the diseased heart 100.

Figure 8:
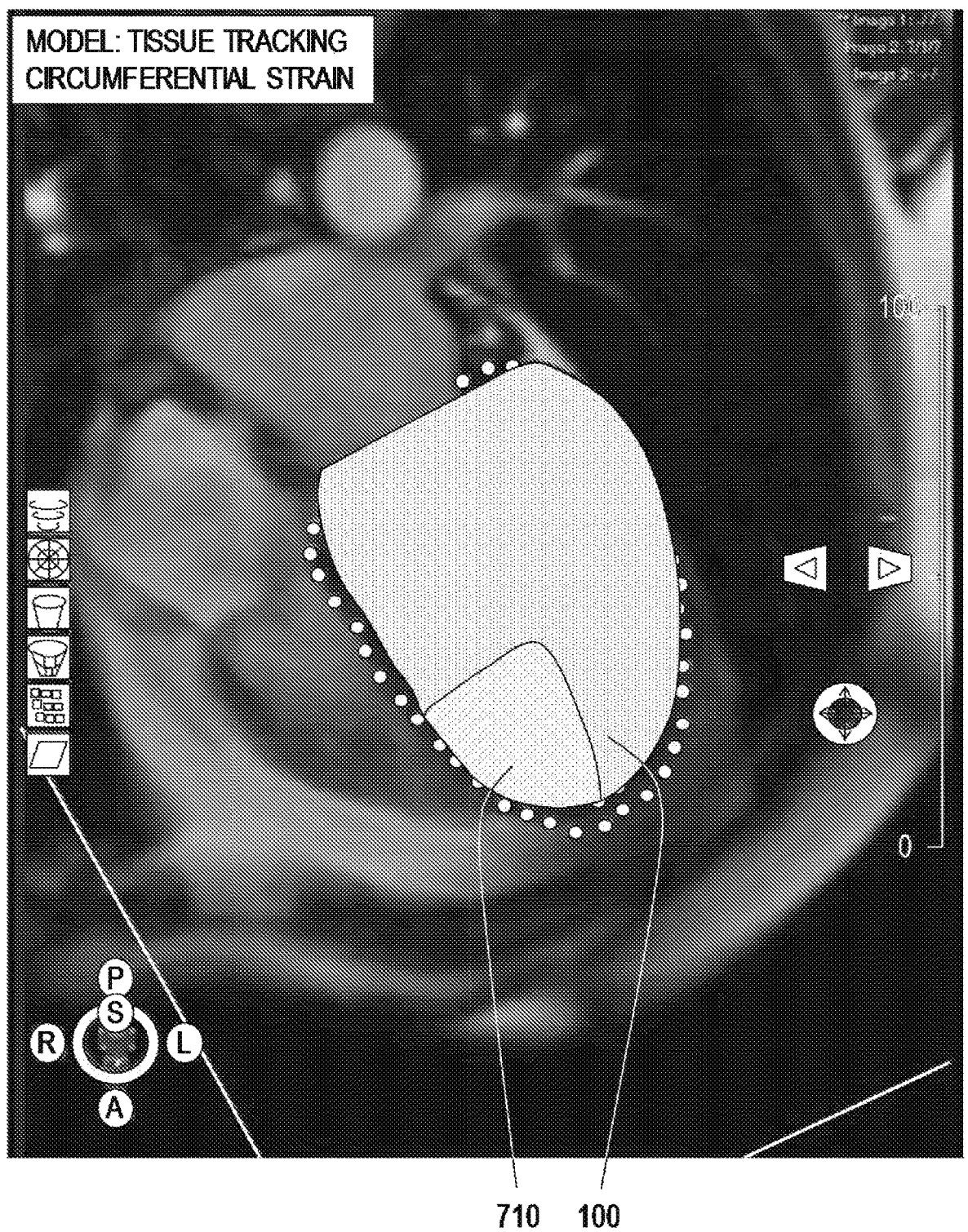
FIG. 8 illustrates an example 3D diseased heart model in which the strain data has been superimposed on a visual representation of the diseased heart.

In operation 540 of FIG. 5, the strain data may be mapped onto corresponding portions of the 3D heart model to form a 3D diseased heart model. The 3D diseased heart model may include the 3D model generated in operation 520 with additional data correlating the provided strain data with physical 3D locations of the diseased heart 100. FIG. 8 illustrates an example 3D diseased heart model in which the strain data has been superimposed on a visual representation of the diseased heart 100. As illustrated in FIG. 8, a particular segment 710 of the diseased heart 100 is identified (e.g., color-coded) to illustrate its relative strain with respect to other segments of the diseased heart. As used herein, the "3D diseased heart model" may include some, but not necessarily all, of the physical characteristics of the diseased heart 100 and the strain data. Though the 3D diseased heart model includes characteristics of the heart encompassing three dimensions and the strain data, the 3D diseased heart model is not limited to a visual model. The 3D diseased heart model may include any combination of data which can represent the physical characteristics of the heart coupled with the strain estimates of the diseased heart 100 in three dimensions.

In composing the 3D diseased heart model, the method may utilize the 3D heart model as a guide to interpret the imaging data and the strain data that is provided. Stated another way, the method may start with the 3D heart model which is then customized based on the physical characteristics determined from the imaging data and/or strain data. As such the 3D heart model and/or the 3D diseased heart model is not necessarily an exact match for the diseased heart 100 of the patient. The various 3D models are intended to represent those portions of the diseased heart 100 that are relevant to the ventricular support device. As a result, the 3D heart model and/or the 3D diseased heart model may map/represent some, but not all, of the physical characteristics of the diseased heart 100.

Figure 9A:
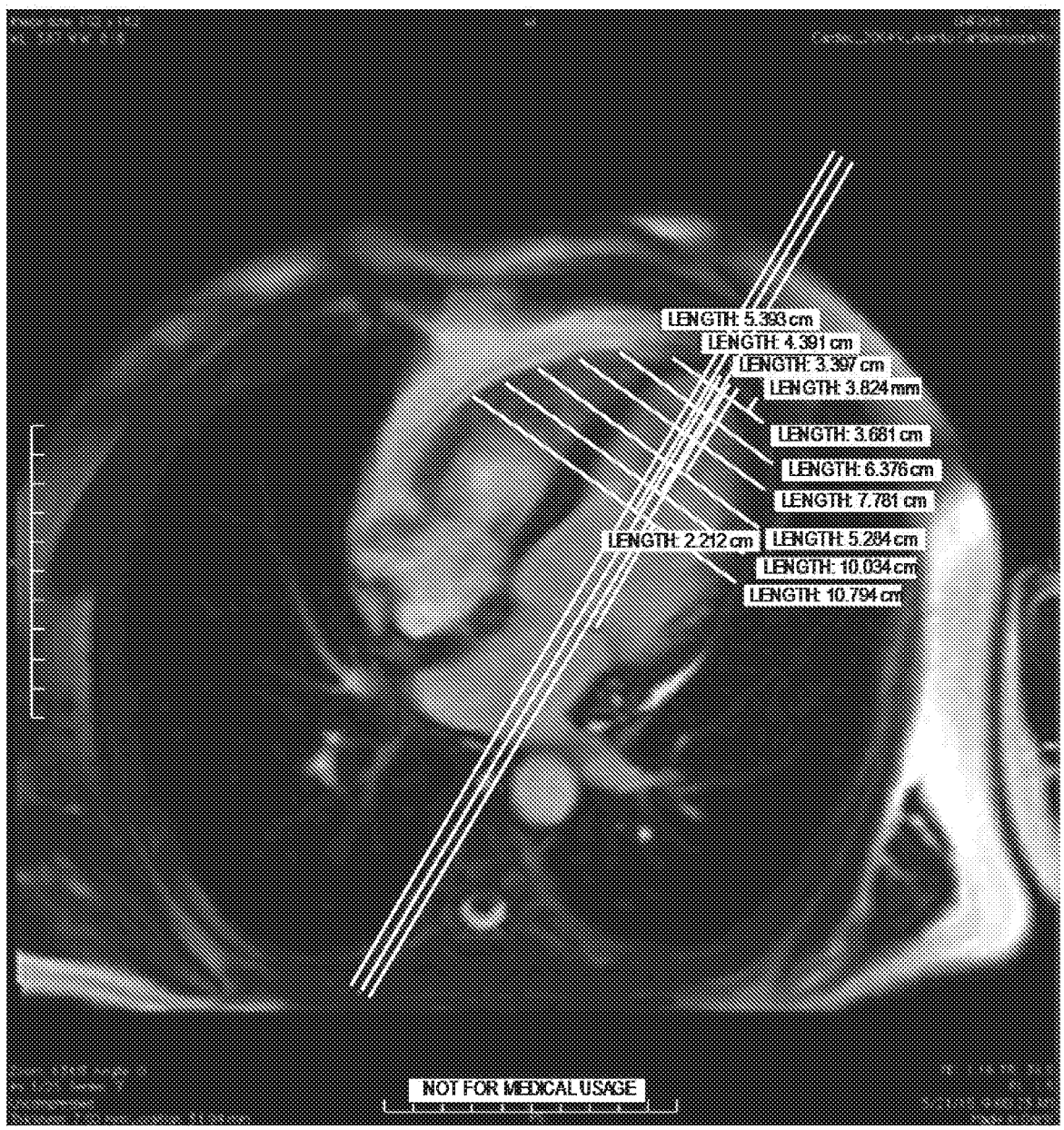
FIGS. 9A and 9B illustrate a determination of the physical dimensions of a heart based on imaging data.
Figure 9B:
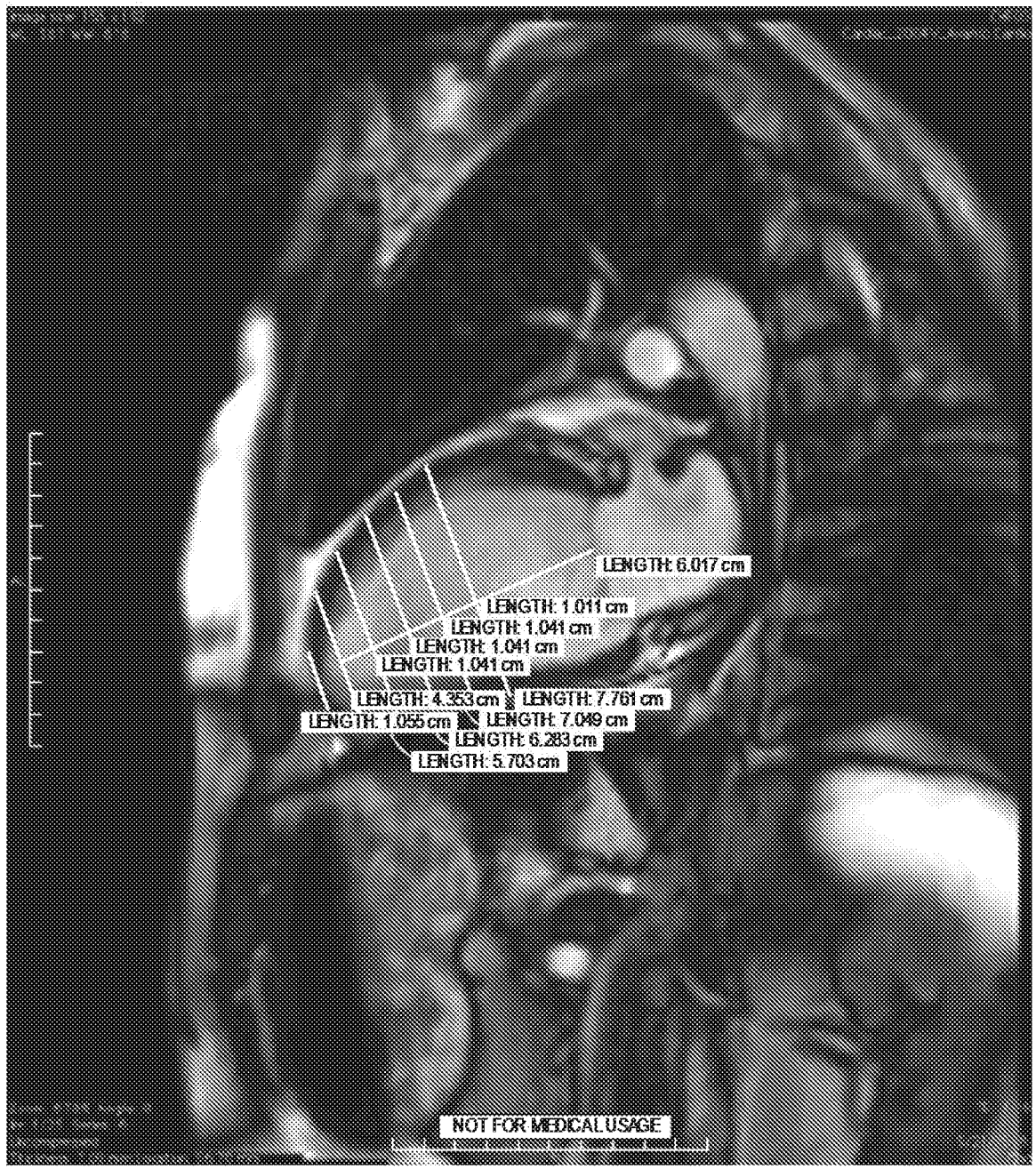
Figure 9C:
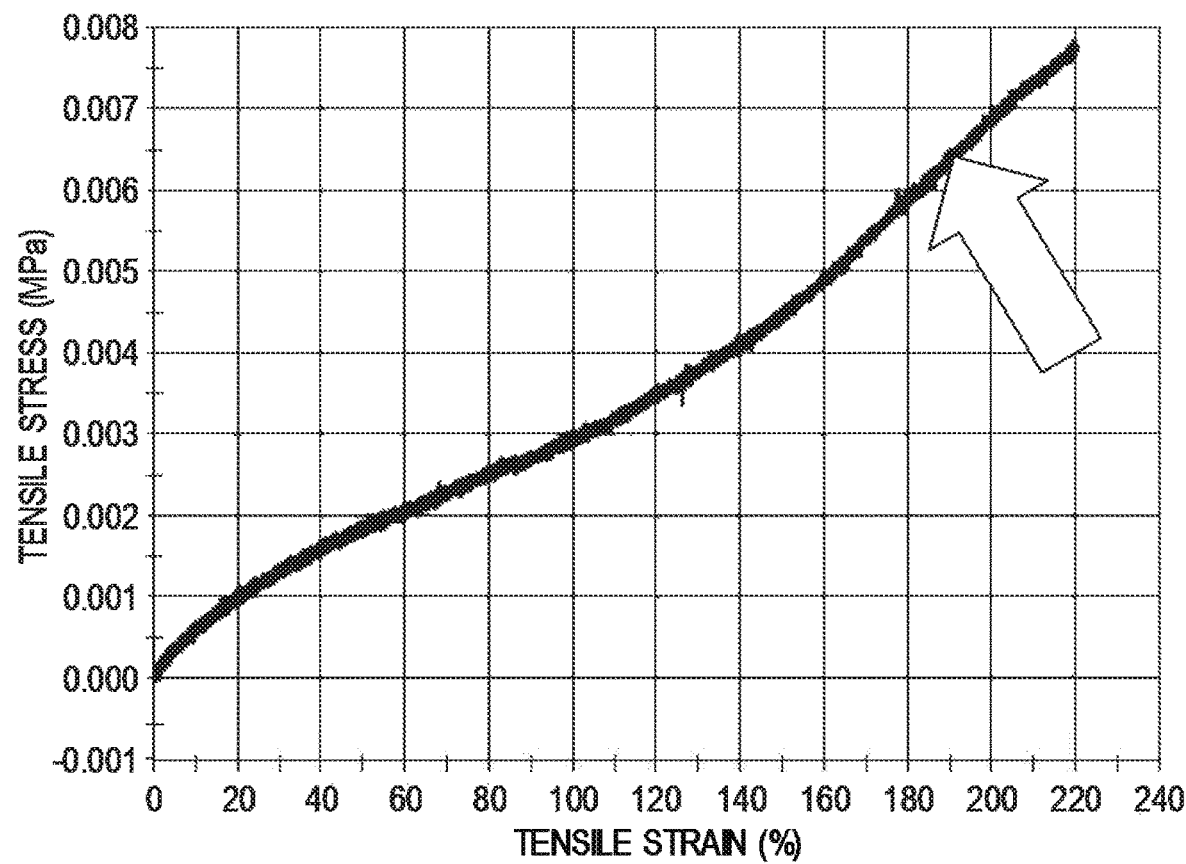
FIG. 9C is an example chart of a stress-strain curve used to determine a strain estimate for a diseased heart.

The 3D diseased heart model as taught herein may be formed by corresponding specific strain estimates to specific locations of the diseased heart 100. For example, based on the imaging data provided in operation 510, estimates of the physical dimensions of the various sections of the diseased heart 100 may be developed. For example, as illustrated in FIGS. 9A and 9B, the 3D heart model may include the circumference of the chambers of the heart that is customized for a particular patient based on the provided image data. Using that customized 3D heart model, it may be determined, for example, that a particular heart has an LVEDP of 10 mmHg, with a chamber radius of 3 cm and a wall thickness of 6.17 mm. Using the equation described herein with respect to FIG. 4, a transmural pressure of 48.6 mmHg (0.0065 MPa) may be calculated. Using stress-strain curves for cardiac muscle, as illustrated in FIG. 9C, the tensile strain at that location of the heart can be determined. Repeating this procedure for multiple strain values (such as those illustrated in FIG. 7) can result in a mapping for strain values across the physical dimensions of the diseased heart 100.

Once the mapping of strain values to physical locations of the diseased heart has been determined, the method may continue with operation 550 where, based on the 3D diseased heart model, a model may be formed of a ventricular support device that is configured to provide support customized for the diseased heart. Stated another way, the ventricular support device may be configured to provide increased support to those areas of the diseased heart 100 which have been determined to experience increased strain relative to those portions of the same diseased heart 100 which undergo less strain. Because the underlying data used in forming the model of the customized ventricular support device is based on both the imaging data and the strain data, the ventricular support device may be customized for a particular patient or subject.

In some embodiments, the model of the customized ventricular support device may be formed to allow space and/or reduced pressure for the locations of the cardiac blood vessels and other particular structures identified as part of the imaging data.

Though the model of the ventricular support device may be based on the provided imaging data and strain data, other data may be used to assist with forming the model. For example, treatment data related to the patient's condition may be used to alter various configurations of the ventricular support device. For example, data including blood flow, blood analysis, and/or acoustic measurements may also be included as treatment data for the diseased heart. In some embodiments, indications of pain from the patient and/or communicated perceptions of energy levels may be used to alter the model of the ventricular support device to be more aggressive or more conservative based on medical judgment. In some embodiments, the New York Heart Association (NYHA) heart failure classification may be applied to the patient, and the relevant classification used as input to the model of the diseased heart and/or ventricular support device. Other objective values such as, for example, the ejection fraction of left ventricle, may also be incorporated in the assessment of the cardiac function.

Figure 10:
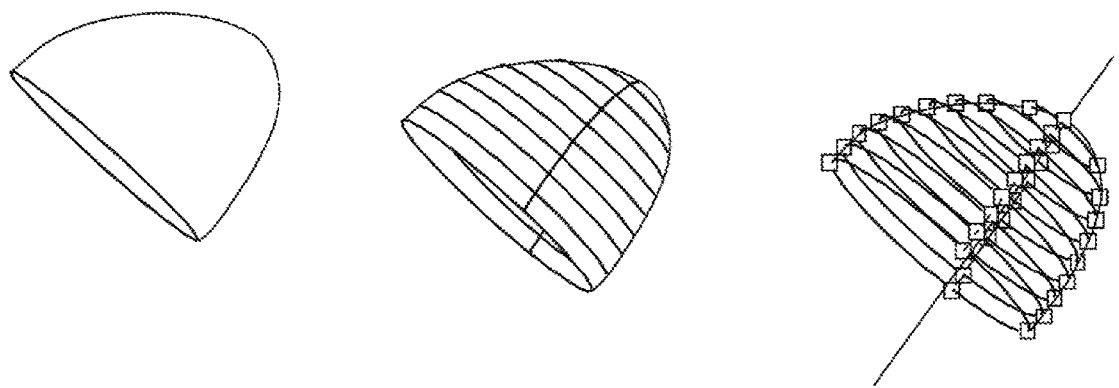
FIG. 10 is an example of a digital representation of a customized ventricular support device model.

As illustrated in FIG. 10, a digital representation of a customized ventricular support model may be divided into layers and indicate seams(s) where printed sheet(s) adjoin.

In some embodiments, the customized ventricular support model may be configured as a lattice mesh. In some embodiments, the mesh may be a diamond mesh. The mesh may be configured to wrap around and/or surround the heart muscle of the diseased heart to provide the support indicated by the 3D diseased heart model. Various designs for the customized ventricular support model can be used.

The method illustrated in FIG. 5 may continue at operation 560 where the model of the ventricular support device may be converted to a digital 3D print file. The digital file may be used as instructions to be provided to a 3D printer so as to generate a physical ventricular support device based on the model of the ventricular support device. As used herein, a "3D print file" may be any series of instructions that can be provided to a 3D printer device to generate the ventricular support device. In some embodiments, the machine may be a 3D printer capable of printing using a biodegradable material. In some embodiments, the biodegradable material may include poly(L-lactide-co-caprolactone) (PLCL).

A 3D printer may use instructions provided in, for example, a print file to construct a physical scaffold using, for example, additive deposition of material. The 3D printer may use, for example, fused deposition modeling, selective laser sintering, inkjet 3D printing, laminated object manufacturing, photopolymerization, magnetic bioprinting, stereolithography, and/or direct cell extrusion, though the embodiments taught herein are not limited thereto. The print file may provide instructions which indicate to the 3D printer which and how much material is to be deposited, and in what locations, to generate the physical ventricular support device. It will be understood that while the present method describes the generation of the 3D print file, the actual creation of the physical ventricular support device (e.g., the use of the 3D print file by a 3D printer) may take place at a later time and/or location.

Figure 11A:
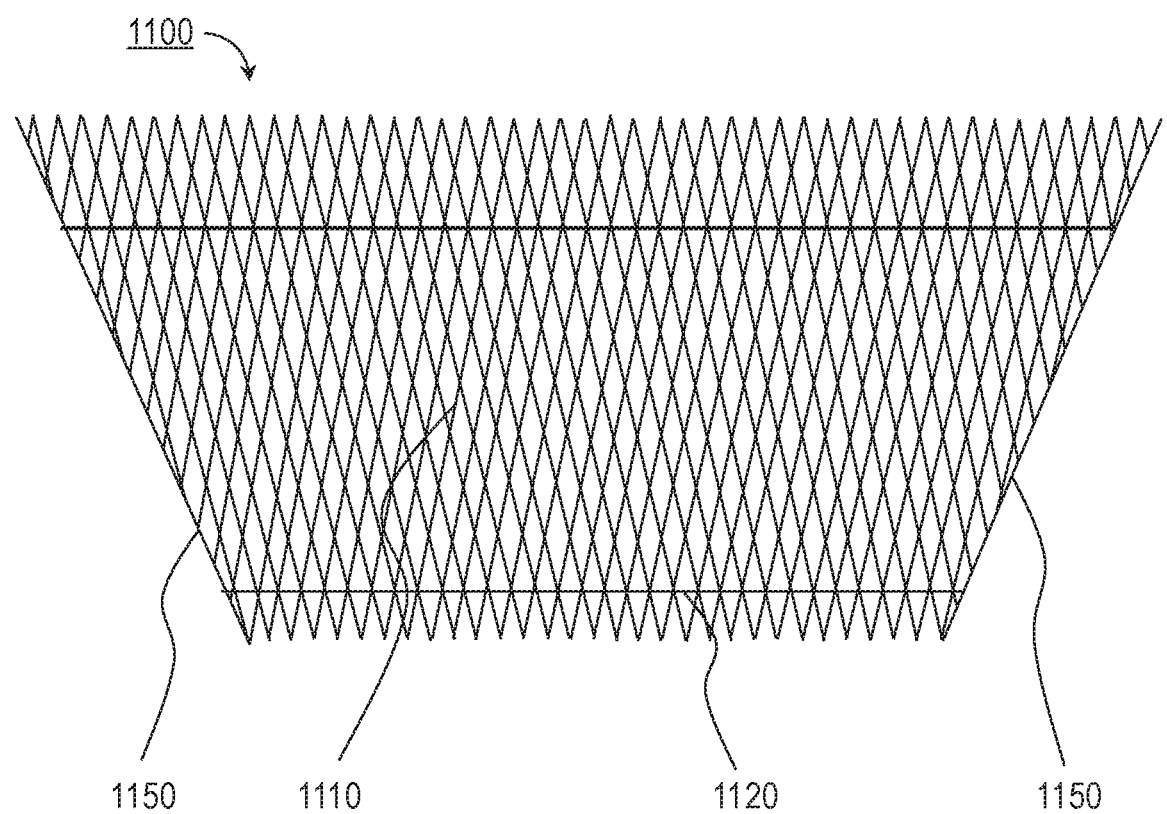
FIG. 11A illustrates another formed sheet design for a ventricular support device according to some embodiments taught herein.

FIG. 11A illustrates a formed sheet design for a ventricular support device 1100 to be created from the generated model according to some embodiments taught herein. As illustrated in FIG. 11A, the ventricular support device 1100 may include a mesh design 1110. The mesh design 1110 may include diamonds, as illustrated in FIG. 11A, but the embodiments taught herein are not limited thereto. In some embodiments, the mesh design may include circles, ellipses, polygons, and/or other shapes, including combinations thereof. The mesh design 1110 may include a support structure 1120 that may provide additional support for the mesh.

As shown in FIG. 11A, the support structure 1120 may include a horizontal structure connecting portions of the mesh design 1110. The support structure 1120 may provide additional lateral support for the mesh design 1110 and may assist in maintaining the overall tensile strength of the mesh 1110. The desired tensile strength of the ventricular support device 1100 will vary based on each diseased heart for which it is designed. A patient with markedly severe heart failure may need more tensile strength of the wrap as compared to another patient with heart disease that is less severe. In some embodiments, the tensile stress may be about 10 mmHg for an average patient, but the embodiments taught herein are not limited thereto. Though illustrated as dual horizontal elements, it will be understood that the support structure 1120 may be composed of a single horizontal element, or more than two horizontal elements. Also, though illustrated as horizontal elements, the embodiments taught herein are not limited thereto. In some embodiments, the support structure 1120 may include horizontal elements, vertical elements, diagonal elements, and/or combinations thereof.

In some embodiments, the ventricular support device 1100 may include a biodegradable material. In some embodiments, the ventricular support device 1100 may include poly(L-lactide-co-caprolactone) (PLCL). In some embodiments the PLCL weight ratio may be approximately 75:25 LA:CL, though other weight ratios are possible. For example, in some embodiments, the weight ratios may be approximately 50:50, 70:30, 80:20 or 90:10, though the embodiments taught herein are not limited thereto. In some embodiments, the ratio and/or molecular weight of the PLCL used in the ventricular support device 1100 may not be uniform across the ventricular support device 1100. That is to say that different portions of the ventricular support device 1100 may be composed of different compositions of PLCL. The composition level of the PLCL may be selected responsive to a level of support needed at a particular location of the ventricular support device 1100.

Similarly, other biodegradable materials may be used. For example, other possible materials to be used for the ventricular support device 1100 may include poly(glycolide-co-caprolactone) (PGCL), and poly(lactic acid-co-dioxanone) (PLDO), poly(butylene succinate) (PBS), poly(p-dioxanone) (PDO), homopolymers such as poly-trimethylene carbonate (PTMC), and copolymers and terpolymers thereof. In some embodiments, the materials used in the ventricular support device 1100 may not be uniform across the ventricular support device 1100. That is to say that different portions of the ventricular support device 1100 may be composed of different materials. The materials used may be selected responsive to a level of support needed at a particular location of the ventricular support device 1100.

In some embodiments, the ventricular support device 1100 may include a biodegradable elastomeric material. In some embodiments, the elastomeric material may include a crosslinked elastomeric material. For example, the material may include a crosslinked elastomeric polyester, such as polycaprolactone (PCL) (e.g., linear crosslinked PCL). Any suitable crosslinking element(s) of varying molecular weights may be used (for example, polyurethane oligomers formed from the reaction of an isocyanate and a polyol), as long as the resulting purified polymer is both biocompatible and biodegradable. See also US 2006/0233857 to Amsden et al.; and U.S. Patent Application Publication No. 2009/0047256 to Bettinger et al.

For extrusion-based 3D printing, in some embodiments the material may be room-temperature extruded as a mixture of precursor functionalized polymer backbone molecules, crosslinking oligomers, and an ultraviolet (UV)-sensitive free radical initiator. When the material is extruded onto the substrate, a UV lamp (which could be integrated in the printer) can irradiate and crosslink the printed filament into a solid elastomeric material, during and/or subsequent to the extruding. The material may also be 3D printed with digital light processing (DLP) printing, in which a resin containing all precursors is illuminated by a UV 3D projection of the printed object, rapidly curing it.

In another approach, an already crosslinked polymer can be mixed with appropriate organic solvent(s) (such as dimethyl sulfoxide (DMSO) and optionally water), and the resulting mixture extrusion printed. This may involve printing at room temperature, or it may involve printing in a cooled environment onto a cooled substrate platform. In the latter case, the ambient temperature may be cooled to less than room temperature, and the platform may be cooled to less than 0 degrees Celsius, for example. In this case, the material will solidify upon contact with the cooled substrate, and the process can continue until the printing is completed. In some embodiments, this approach may also use rotary evaporation or a similar method to reduce the concentration of solvent to a low enough percentage for stable extrusion printing. See also Kirchmajer et al., "An overview of the suitability of hydrogel-forming polymers for extrusion-based 3D-printing," J. Mater. Chem. B, 2015, 3, 4105-4117; Chung et al., "Bio-ink properties and printability for extrusion printing living cells," J. Biomaterials Sci.: Polymer Edition, 2013, 1(7):763-773; and Guo et al., "Solvent-Cast Three-Dimensional Printing of Multifunctional Microsystems," Small, 2013, 9(24): 4118-4122.

Figure 11B:
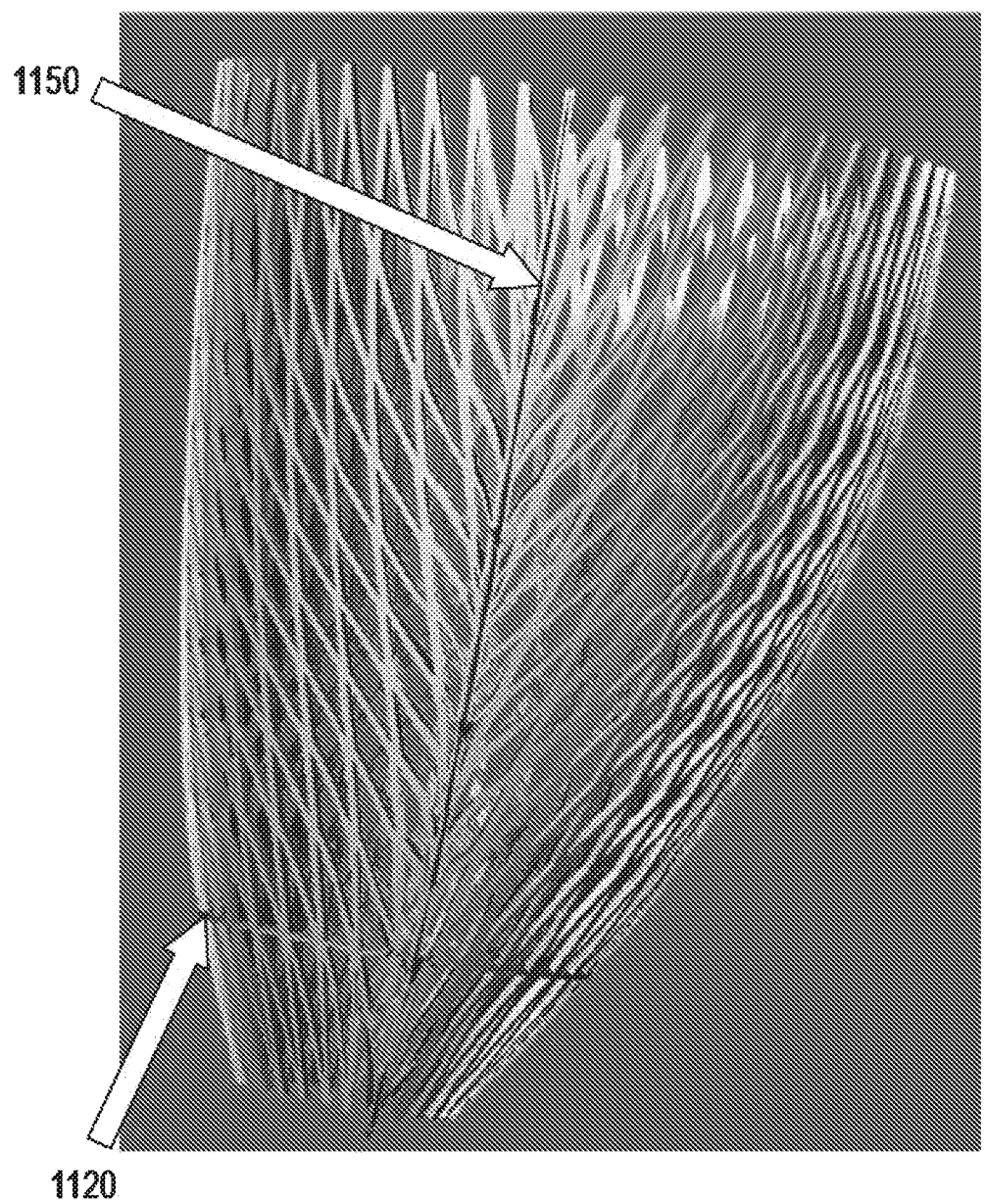
FIG. 11B illustrates ends of the formed sheet design of FIG. 11A being connected to form a ventricular support device that can surround a diseased heart.

As illustrated in FIG. 11A, in some embodiments, the ventricular support device 1100 may be constructed as a flat mesh sheet which is configured to be joined at opposing ends 1150 to form an enclosing structure. For example, as illustrated in FIG. 11B, ends 1150 of the formed sheet design may be joined to form the ventricular support device 1100. In some embodiments, opposing ends 1150 of the ventricular support device 1100 may be joined to form a conical frustum shape. The opposing ends 1150 may be connected to one another via a mechanical and/or adhesive operation. For example, in some embodiments, a suture or other connective mechanism may be used to connect the opposing ends 1150 to one another. In some embodiments, the opposing ends 1150 may be glued, melted, and/or sealed together, though the embodiments taught herein are not limited thereto. It will be understood that multiple mechanisms may be used to connect the opposing ends 1150 to one another without deviating from the embodiments taught herein.

Figure 11C:
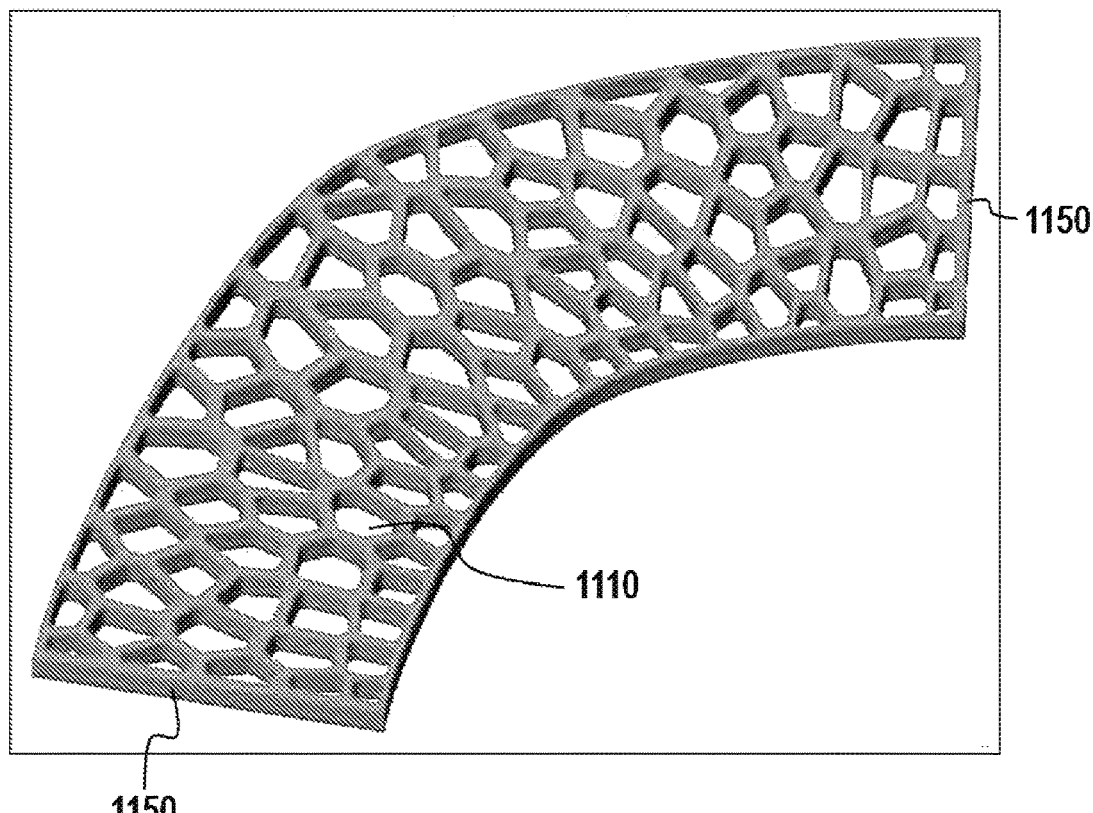
FIG. 11C illustrates a formed sheet design for a ventricular support device according to some embodiments taught herein.
Figure 11D:
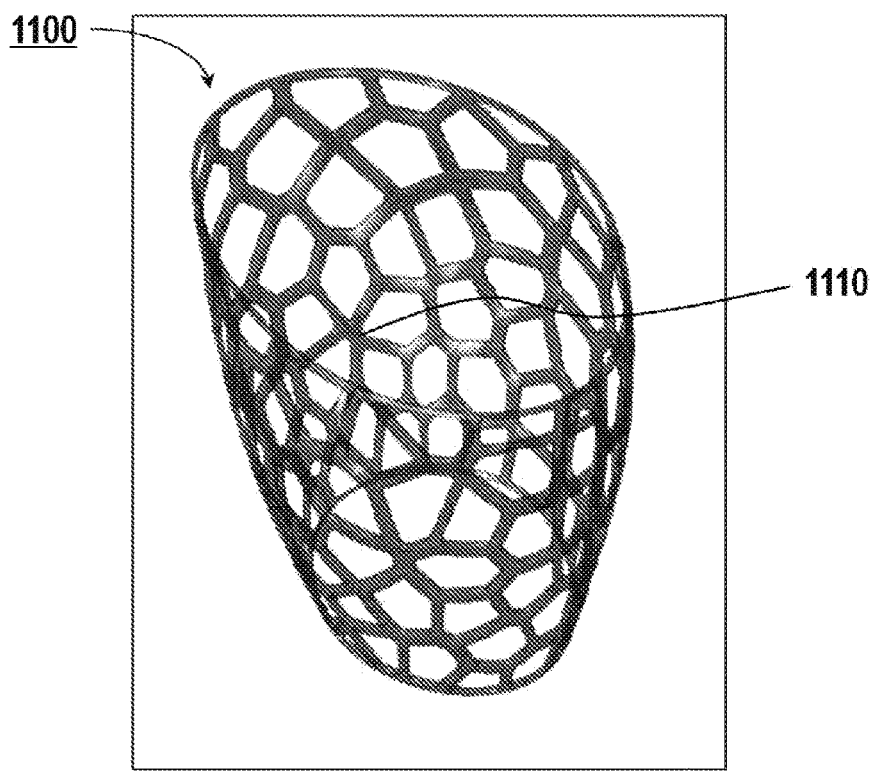
FIG. 11D illustrates ends of the formed sheet design of FIG. 11C being connected to form a ventricular support device that can surround a diseased heart.

Though shown as a symmetrical sheet in FIG. 11A, it will be understood that other designs for the mesh design 1110 are possible. In some embodiments, the mesh design 1110 may be asymmetrical. In some embodiments, as illustrated in FIG. 11C, the mesh design 1110 may be a Voronoi pattern. The Voronoi pattern is a mathematically-driven pattern that may provide more stability to particular areas of the device while using less material. As illustrated in FIG. 11C, the asymmetrical pattern of the mesh design 1110 may allow the formation of an asymmetrical ventricular support device 1100 when the ends 1150 are joined together. FIG. 11D illustrates ends 1150 of the formed sheet design of FIG. 11C being connected to form a ventricular support device 1100.

Though illustrated as a flat sheet design which may be joined, it will be understood that other configurations are available. In some embodiments, the ventricular support device 1100 may be configured as a wrap without requiring additional fastening. In other words, the generated 3D print file may configure the printing of a ventricular support device 1100 in a vertical manner that is already in a wrap format which does not require additional fastening.

As described herein, the ventricular support device 1100 may be customized for a particular diseased heart 100. In some embodiments, the ventricular support device 1100 may be configured to provide a particular uniform support level that is customized to a particular diseased heart 100. In other words, based on the imaging data of the heart and the resulting customized 3D heart model, a specific level of uniform pressure may be determined for the benefit of the patient or subject. The level of uniform pressure may be used in forming the ventricular support device 1100 and the mesh design 1110.

In some embodiments, the ventricular support device 1100 may be configured to provide non-uniform support such that particular portions of the ventricular support device 1100 provide greater or less support than other portions of the ventricular support device 1100. As a result, particular portions of the mesh 1110 of the ventricular support device 1100 may be configured to provide additional support. FIGS. 12A-D illustrate embodiments of a mesh design 1110 for a customized ventricular support device 1100 according to some embodiments taught herein. For example, FIG. 12A includes a portion 1160 in which individual strands of the mesh are reinforced. The portion 1160 may be a reinforced portion 1160 and/or may include material with a higher tensile strength than other portions of the mesh 1110. In some embodiments, the reinforced portion 1160 may include additional amounts of the material used for other portions of the mesh 1110. In some embodiments, the reinforced portion 1160 may include a different material than other portions of the mesh 1110. The reinforced portion 1160 may correspond to a strained portion of the diseased heart in which additional support is necessary, and may be configured to support the strained portion of the heart when the ventricular support device 1100 is in place.

Though the portion 1160 is discussed above as a reinforced portion of the ventricular support device 1100, other configurations are possible. In some embodiments, the portion 1160 may be configured to be less tensile than other parts of the ventricular support device 1100. In other words, the portion 1160 may be a more elastic portion of the ventricular support device 1100. Such a configuration may be appropriate when the corresponding portion of the heart does not require as much support from the ventricular support device 1100 as other portions of the heart.

Figure 12A:
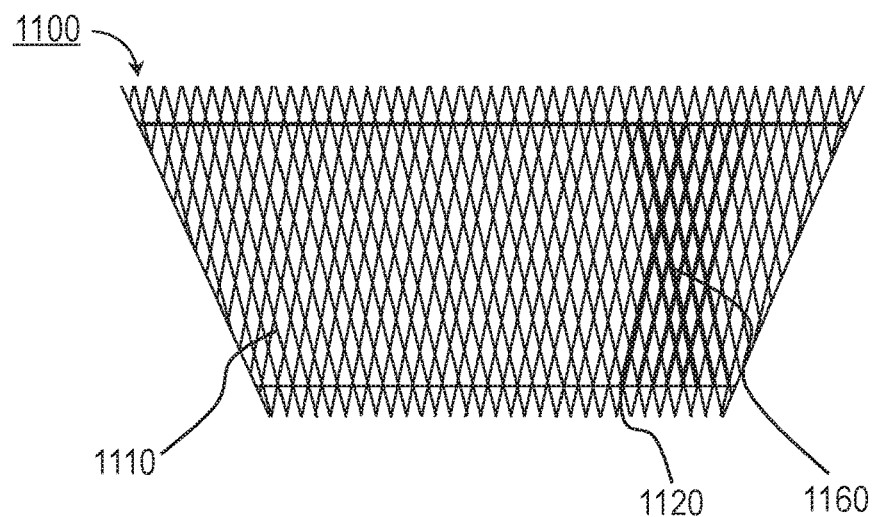
FIGS. 12A-D illustrate embodiments of a mesh design for a customized ventricular support device according to some embodiments taught herein where there are segments of variable support.
Figure 12B:
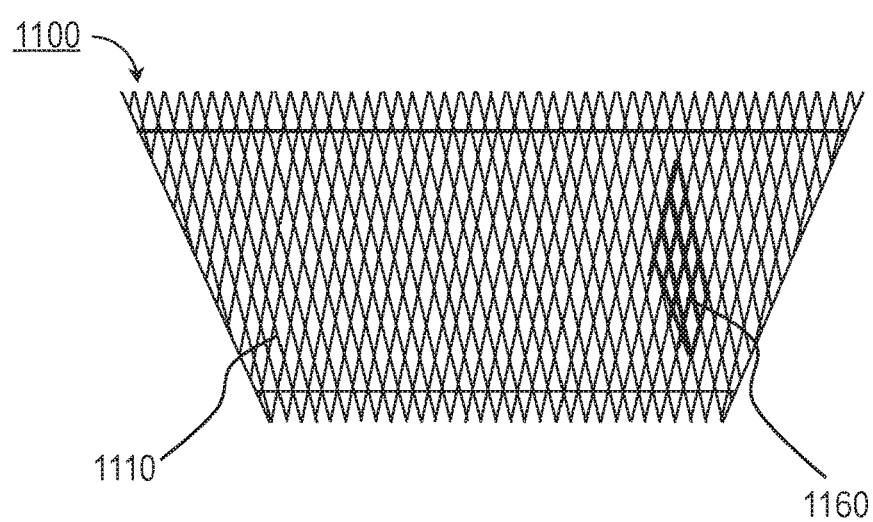

In FIG. 12A, the individual strands of the reinforced portion 1160 may connect to the support elements 1120 of the mesh 1110. In some embodiments, as illustrated in FIG. 12B, the portion 1160 may include segments of individual strands of the mesh 1110. The portion 1160 illustrated in FIG. 12B may be composed of thicker strands of the mesh 1110, or may include the addition of a different type of material or a combination of materials within the portion 1160. As described with respect to 12a, the portion 1160 of FIG. 12B may be more or less elastic than other portions of the mesh 1110.

Figure 12C:
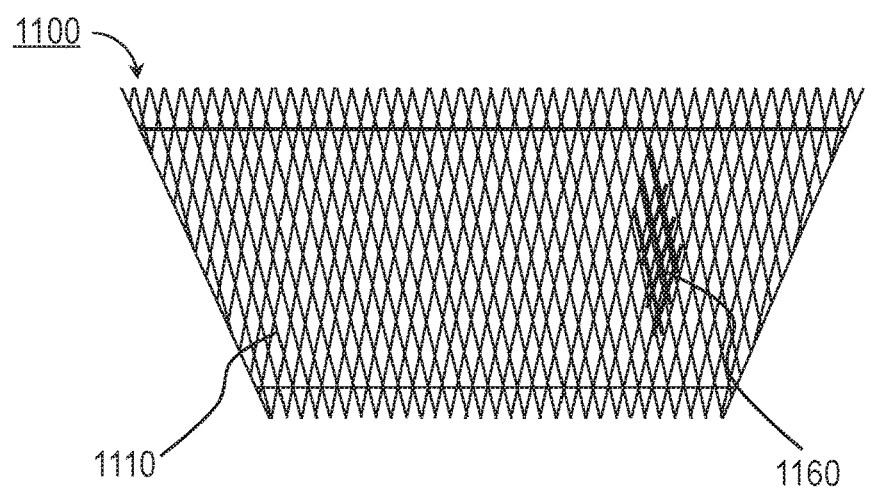

FIG. 12C illustrates an embodiment in which the portion 1160 is constructed by increasing the density of the number of strands of the mesh 1110 within the portion 1160. In other words, additional strands of material may be provided within the portion 1160 to create a subset of the mesh 1110 that includes a denser configuration of mesh strands. The additional mesh strands within the portion 1160 of the mesh 1110 may be composed as the same or different material as the other strands of the mesh 1110.

Figure 12D:
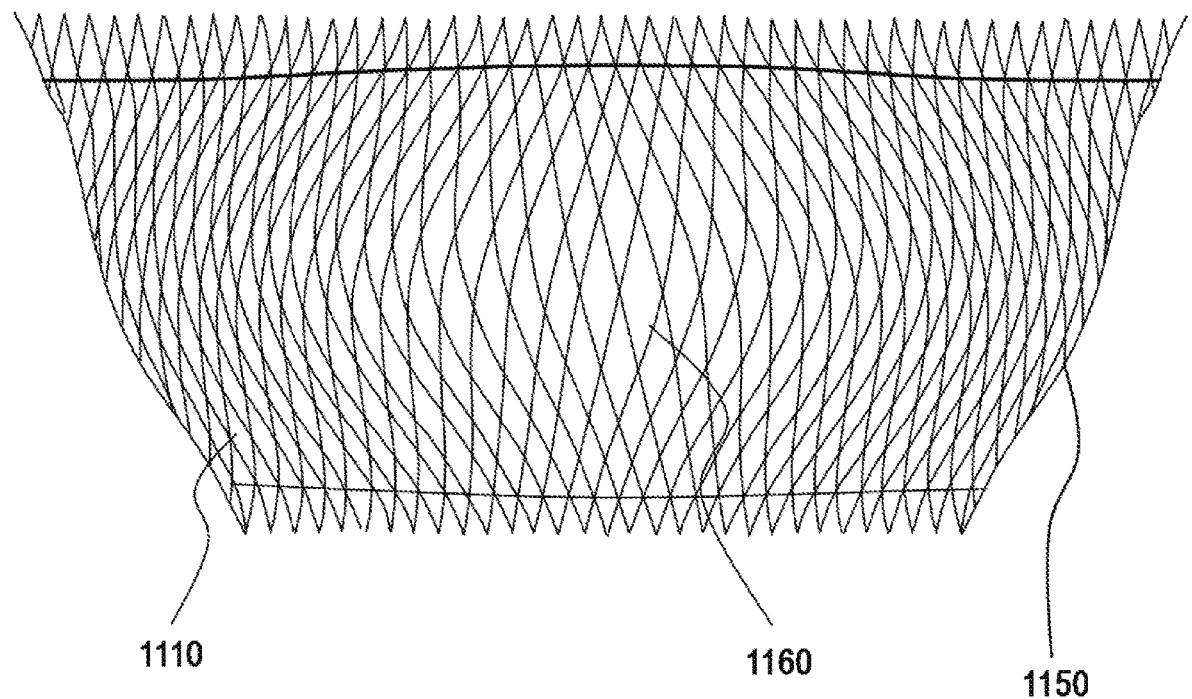
Figure 13:
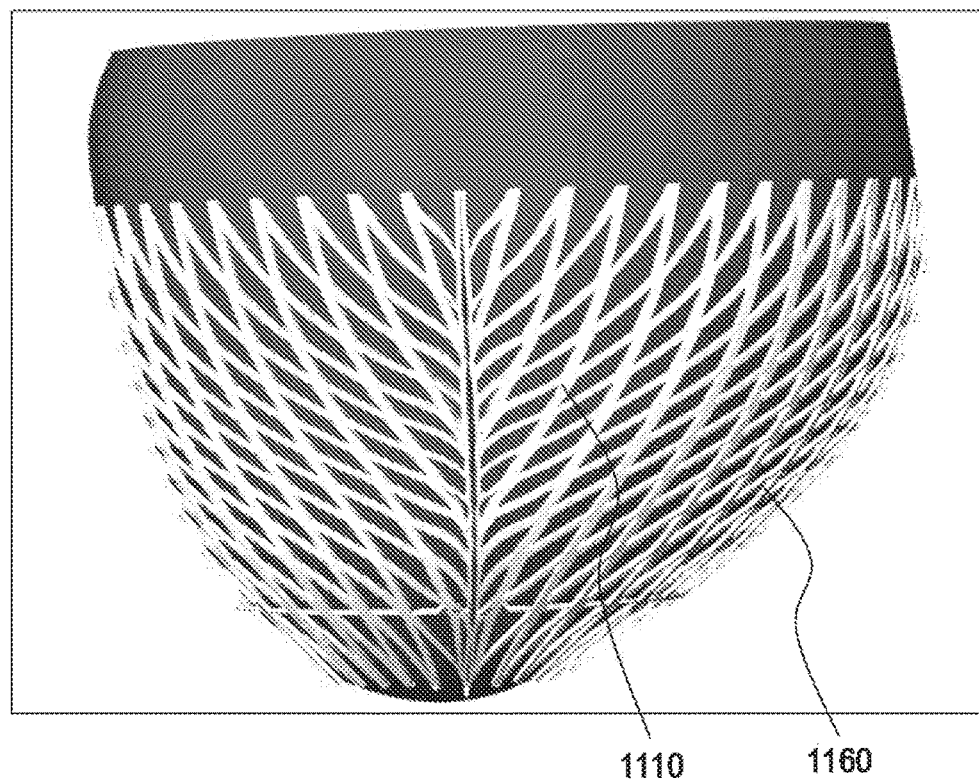
FIG. 13 illustrates a model of a customized ventricular support device in place on a heart.

FIG. 12D illustrates an embodiment in which a portion 1160 of the mesh 1110 is configured to be asymmetrical. The construction of the mesh 1110 within the portion 1160 may be different as compared to other portions of the mesh 1110. For example, individual shapes making up the portion 1160 of the mesh 1110 may be shaped differently than other parts of the mesh 1110. In some embodiments, the portion 1160 may be composed so as to be non-planar with other parts of the mesh 1110. That is to say that the portion 1160 may comprise a bulge in the mesh 1110. As discussed herein, the bulge provided by the portion 1160 may provide greater or lesser support than other parts of the mesh 1110. When opposing ends 1150 of the ventricular support device 1100 are joined (see, e.g. FIG. 11B), the resulting ventricular support device 1100 may have an asymmetrical shape. The asymmetrical shape may match a corresponding asymmetry in the diseased heart. For example, when the asymmetrically-shaped ventricular support device 1100 is placed on the diseased heart, it may correspondingly match and correspondingly support asymmetries in the diseased heart. For example, as illustrated in FIG. 13, when the ventricular support device 1100 is placed on a heart, portion 1160 of the ventricular support device 1100 may contain contours that match the contours of the heart, so that support provided by the ventricular support device 1100 is customized to the diseased heart.

FIGS. 12A-D illustrate multiple ways in which the ventricular support device 1100 can be customized to match the physical contours and strain profiles of a diseased heart, but the embodiments taught herein are not limited thereto. Other methods of constructing the ventricular support device 1100 are possible without deviating from the embodiments taught herein. In some embodiments, the ventricular support device 1100 may be solid, rather than a mesh, or include solid portions in addition to the mesh. Similarly, portions of the ventricular support device 1100 may use combinations of construction, materials, and density to accomplish the customization of the device to match a particular diseased heart.

It will be understood that the variations in the design of the ventricular support device 1100 may be accomplished via corresponding changes to the 3D print file discussed herein with respect to operation 560 of FIG. 5. For example, increases in the density of individual strands of the mesh 1110 of the ventricular support device 1100 may be accompanied by corresponding changes to the 3D print file of operation 560 that configure a 3D printer to construct the ventricular support device 1100. Similarly, in some embodiments, changing materials within the mesh 1110 may be accomplished by sections of the 3D print file which direct the 3D printer to print those portions of the mesh 1110 using different materials. In this way, the 3D print file can indicate how the ventricular support device 1100 is to be customized for a particular diseased heart.

Figure 14:
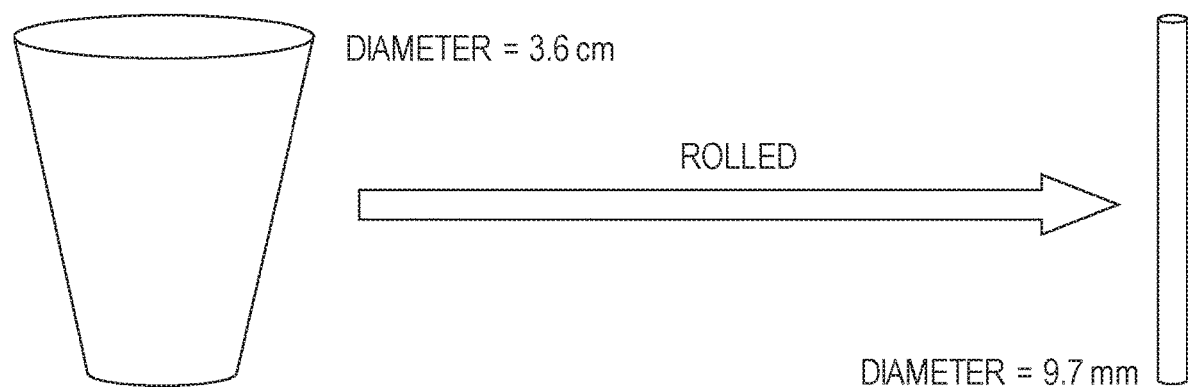
FIG. 14 illustrates a configuration of a ventricular support device that may be rolled for insertion into a patient by laparoscopic surgery.

In some embodiments, the generation of the 3D print file may be customized using particular variables. For example, referring again to FIGS. 5 and 12A, the operation 560 to create a digital file for directing a 3D printer may include specifying a variable representing a particular tensile strength, elasticity, and/or other physical characteristic of a particular customized portion 1160 of the ventricular support device 1100, without specifying the material, and or composition of material to be used. When creating the ventricular support device 1100, this characteristic may be converted to a particular material and/or composition of material that meets the characteristic based on what materials are available. For example, in operation 510 it may be indicated that a particular value of tensile strength X is needed for a particular portion 1160 of the mesh 1110. In a first iteration, the operation 560 may determine that an available 3D printer uses PLCL with a weight ratio of 75:25, and may further determine that achieving the tensile strength X will require a first configuration of the mesh 1110. In a second iteration, the operation 560 may determine that another 3D printer uses PLCL with a weight ration of 80:30, and my further determine that achieving the tensile strength X will require a second configuration, different from the first configuration, of the mesh 1110. In yet a third iteration, the operation 560 may determine that another 3D printer has a plurality of materials available, and my further determine that achieving the tensile strength X will require a third configuration using the plurality of materials, different from the first and second configurations, of the mesh 1110. Thus, the generated digital file for directing a 3D printer device to construct the ventricular support device 1100 may be configured to be customizable not only for the contours of the diseased heart, but also for the specific materials used by a particular 3D printer device. As discussed herein, the ventricular support device 1100 is configured to be placed around the diseased heart. Methods of delivering a ventricular support device are discussed, for example, in U.S. Pat. No. 7,077,802, entitled "Expandable cardiac harness for treating congestive heart failure," filed on Nov. 13, 2003, the entire contents of which are incorporated by reference herein. In some embodiments, in order to minimize impact to the patient and shorten time for healing, the ventricular support device 1100 may be installed laparoscopically. Because, in some embodiments, the ventricular support device 1100 is made of a flexible material, the ventricular support device 1100 may be rolled up to facilitate insertion laparoscopically. By rolling up the ventricular support device 1100, the volume of the ventricular support device 1100 is reduced so that it can be inserted into the patient within a smaller access point. FIG. 14 illustrates how the ventricular support device 1100 may be rolled up. In some embodiments, the ventricular support device 1100 can be converted from an object having a 3.6 cm diameter to an object having a 9.7 mm diameter for insertion.

Figure 15A:
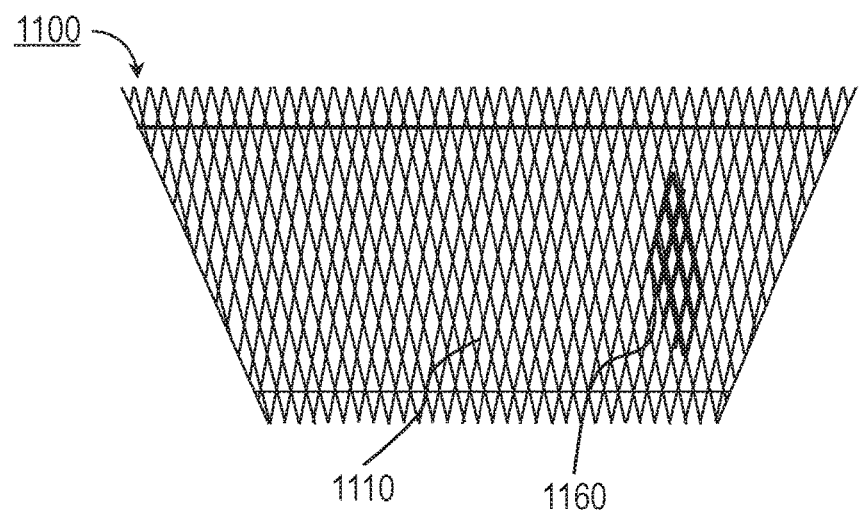
FIGS. 15A-B illustrate index structures that may be used for identifying particular portions of the ventricular support device for placement into a diseased heart.
Figure 15B:
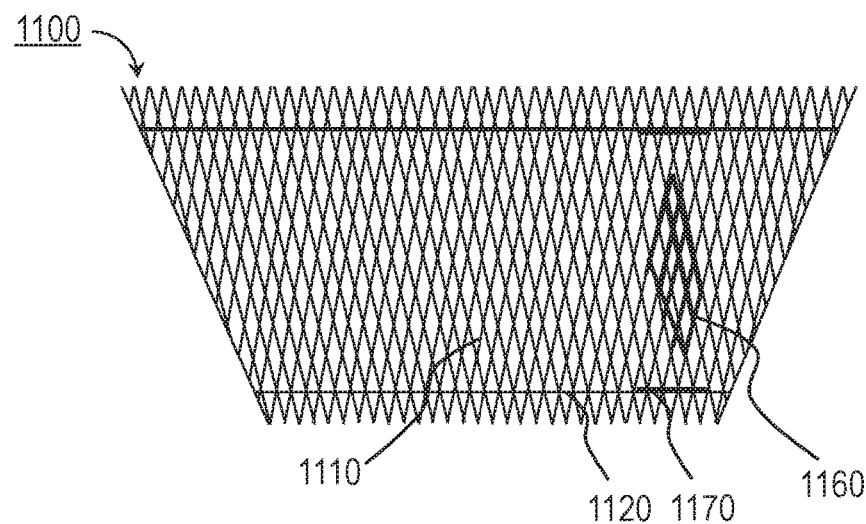

FIGS. 15A-B illustrate index structures that may be used to identify customized portions 1160 of the ventricular support device 1100. Because portions of the ventricular support device 1100 may be customized to particular segments of the diseased heart, the index structures can assist a surgeon to correctly align the ventricular support device 1100 during insertion. For example, as shown in FIG. 15A, a portion 1160 may be constructed to have a different color than other parts of the mesh 1110. Though only a single portion 1160 is illustrated in FIG. 15A, it will be understood that other portions 1160 may be present, and that other colors and/or patterns may be used. That is to say that a plurality of portions 1160 may use various combinations of colors to highlight the location of these portions 1160, and different portions 1160 may use different colors and/or patterns so as to differentiate one portion 1160 from another. Though color is described with respect to FIG. 15A, it will be understood that other visual indicators are possible. For example, in some embodiments, luminescence may be used. In some embodiments, a texture of the mesh 1110 may indicate the individual portions 1160.

As illustrated in FIG. 15B, markers 1170 may also be added to external edges of the mesh 1110 as part of the index structures. The markers 1170 may indicate the relative location and/or width of the customized portions 1160 within the mesh 1110. The markers 1170 may include portions of the mesh 1110 that are configured to be a different color and/or texture from other parts of the mesh 1110. The markers 1170 may be placed near the edge of the ventricular support device 1100 to assist in alignment during insertion. For example, the markers 1170 may be placed on the support element 1120, but the embodiments taught herein are not limited thereto. As illustrated in FIG. 15B, the markers 1170 may be used in conjunction with other visual indicators for proper insertion. In some embodiments, the portions 1160 themselves may not include other visual indicators such as color/texture and only the markers 1170 may be used.

During laparoscopic insertion, the index structures and/or markers may be seen with a laparoscopic camera, intraoperative MRI, intraoperative CT, and/or intraoperative ultrasound imaging, such as those used in neurosurgery. See Prada et al., "Fusion imaging for intraoperative ultrasound-based navigation in neurosurgery," J. Ultrasound 2014 Sep. 17(3):243-251. In some embodiments, the ventricular support device (e.g., index structures and/or markers) include a magnetically opaque material and/or contrast agent detectable with MRI. See U.S. Pat. No. 7,943,161 to Carlgren et al., which is incorporated by reference herein.

It will be understood that the visual indicators and markers discussed herein with respect to FIGS. 15A-b may be included as part of the configuration of the 3D printer file in operation 560 of FIG. 5. In other words, creating the 3D printer file associated with the customized ventricular support device 1100 may include instructions in the 3D printer file to alter the structure of the ventricular support device 1100 to provide the visual indicators for the portions 1160 and/or the markers 1170 when the ventricular support device 1100 is created. In this way, the visual indicators to aid in inserting the ventricular support device will be constructed automatically as part of 3D printing the ventricular support device 1100 and may not require subsequent post-processing to add them.

System and/or component operation according to some embodiments may be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the desired operations.

Figure 16:
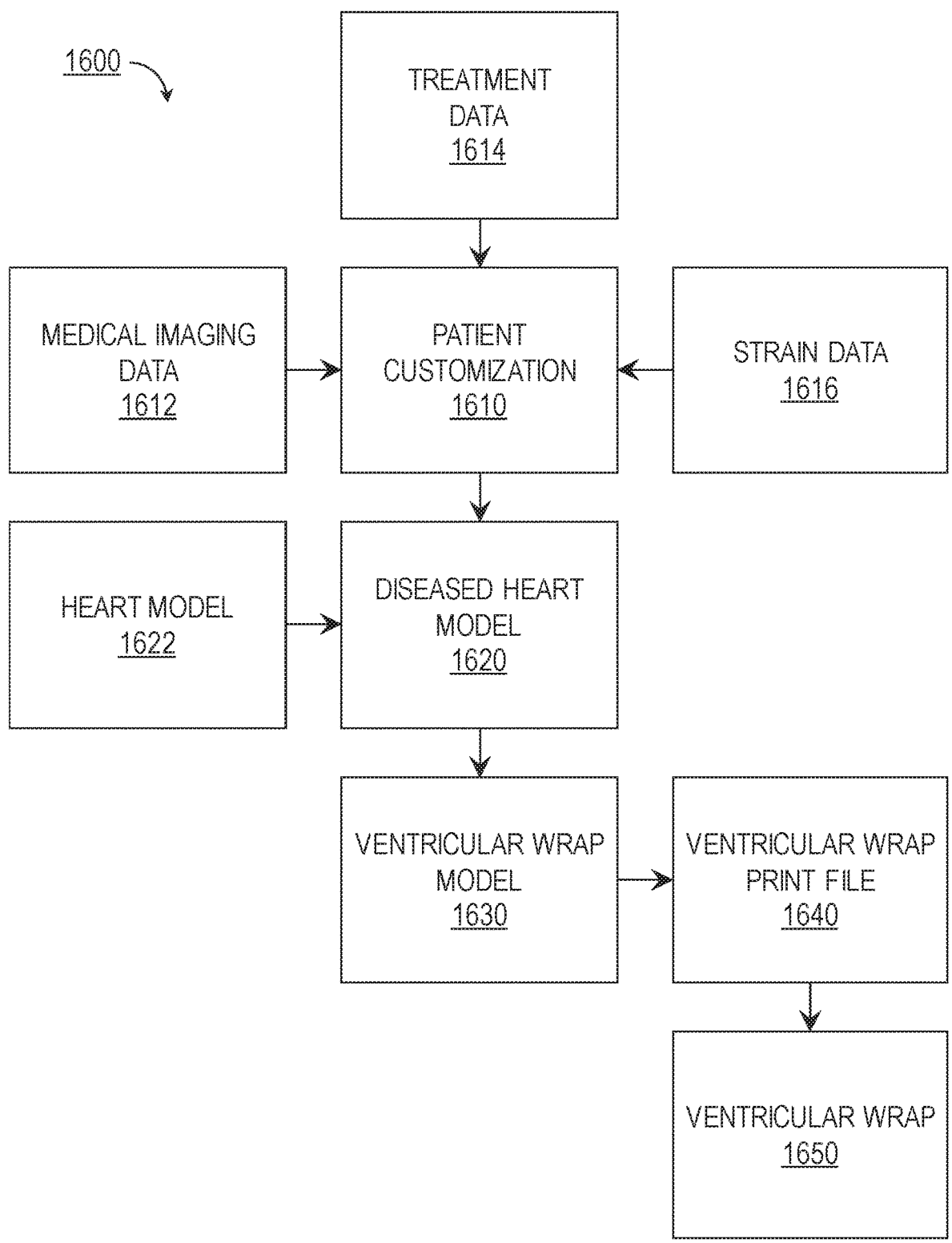
FIG. 16 is a block diagram of a system useful for implementing portions of the method of FIG. 5.

FIG. 16 is a block diagram of a system 1600 useful for implementing portions of the method of FIG. 5. As illustrated in FIG. 16, the system 1600 may include a patient customization module 1610. The patient customization module 1610 may take, as input, medical imaging data 1612 of a patient, treatment data 1614 of the patient, and/or cardiac strain data 1616 of the patient. This input data may be provided, for example, electronically via sensors coupled to a computing device and/or electronically over a computing network coupled to a computing device.

Using the input data, the patient customization module 1610 may generate a set of data customized for the patient. The patient customization module 1610 may execute on a processor of a computing device. The customized patient data may be combined with a 3D heart model 1622 to form a 3D diseased heart model 1620. The 3D diseased heart model 1620 may represent a model of the patient's heart that includes the physical characteristics of the patient's heart as well as related strain data associated with various portions of the patient's heart.

Based on the 3D diseased heart model 1620, a ventricular wrap model 1630 may be generated. The ventricular wrap model 1630 may be a virtual representation of a ventricular wrap customized for the patient's heart. The ventricular wrap model 1630 may be generated by computer code executing on a processor of the computing device. Similarly, the ventricular wrap model 1630 may be stored in a memory and/or other storage device of the computing device.

Using the ventricular wrap model 1630, a ventricular wrap print file 1640 may be generated. The ventricular wrap print file 1640 may be generated by a processor of the computing device and may be configured to be specific to a specific type or configuration of 3D printer. Once generated, the ventricular wrap print file 1640 may be stored in a memory and/or other storage device of the computing device. In some embodiments, the ventricular wrap print file 1640 may be communicated via a computing network coupled to the computing device.

In some embodiments, a ventricular wrap 1650 may be generated from the ventricular wrap print file 1640. The ventricular wrap 1650 may be printed by a 3D printer using instructions provided by the ventricular wrap print file 1640. In some embodiments, the 3D printer may use biodegradable materials to generate the ventricular wrap 1650. The 3D printer that creates the ventricular wrap 1650 may be connected to the computing device 1700 used to generate the ventricular wrap print file 1640 or may be separate from the computing device 1700.

Figure 17:
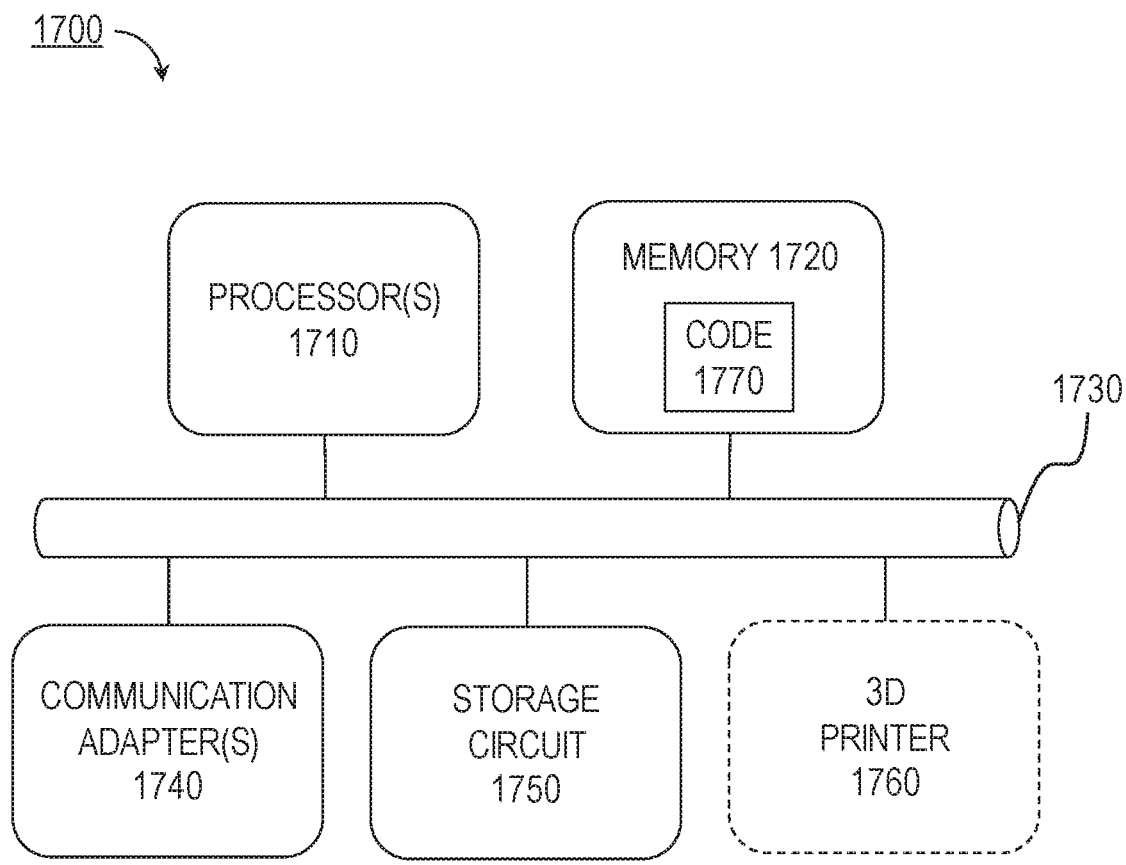
FIG. 17 is a block diagram of a computing device that may be used in the system of FIG. 16.

FIG. 17 is a block diagram of a computing device 1700 for use in the system 1600 of FIG. 16. The computing device 1700 may use hardware, software implemented with hardware, firmware, tangible computer-readable storage media having instructions stored thereon and/or a combination thereof, and may be implemented in one or more computer systems or other processing systems. The computing device 1700 may also utilize a virtual instance of a computer and/or other virtual processing mechanisms. As such, the devices and methods described herein may be embodied in any combination of hardware and software.

As shown in FIG. 17, the computing device 1700 may include one or more processors 1710 and memory 1720 coupled to an interconnect 1730. The interconnect 1730 may be an abstraction that represents any one or more separate physical buses, point to point connections, or both connected by appropriate bridges, adapters, or controllers. The interconnect 1730, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

The processor(s) 1710 may be, or may include, one or more programmable general purpose or special-purpose microprocessors, digital signal processors (DSPs), programmable controllers, application specific integrated circuits (ASICs), programmable logic devices (PLDs), field-programmable gate arrays (FPGAs), trusted platform modules (TPMs), or a combination of such or similar devices, which may be collocated or distributed across one or more data networks. The processor(s) 1710 may be configured to execute computer program instructions from the memory 1720 to perform some or all of the operations and methods for one or more of the embodiments disclosed herein.

The computing device 1700 may also include one or more communication adapters 1740 that may communicate with other communication devices and/or one or more networks, including any conventional, public and/or private, real and/or virtual, wired and/or wireless network, including the Internet. The communication adapter(s) 1740 may include a communication interface and may be used to transfer information in the form of signals between the computing device 1700 and another computer system or a network (e.g., the Internet). The communication adapter(s) 1740 may include a modem, a network interface (such as an Ethernet card), a wireless interface, a radio interface, a communications port, a PCMCIA slot and card, or the like. These components may be conventional components, such as those used in many conventional computing devices, and their functionality, with respect to conventional operations, is generally known to those skilled in the art.

The computing device 1700 may further include memory 1720 which may contain program code 1770 configured to execute operations associated with the methods described herein. The memory 1720 may include removable and/or fixed non-volatile memory devices (such as but not limited to a hard disk drive, flash memory, and/or like devices that may store computer program instructions and data on computer-readable media), volatile memory devices (such as but not limited to random access memory), as well as virtual storage (such as but not limited to a RAM disk).

The computing device 1700 may also include storage 1750. The storage 1750 may be configured to store data generated by the processor(s) 1710 and/or received over the communication adapter(s) 1740. The storage 1750 may also be configured to store the generated ventricular wrap print file 1640 discussed herein. The storage 1750 may include volatile and/or non-volatile storage mechanisms accessible by the one or more processor(s) 1710 and/or the communication adapter(s) 1740.

In some embodiments, the computing device 1700 may also include an optional 3D printer 1760. The 3D printer 1760 may be configured to print a ventricular support device 1100 based on instructions contained in the ventricular wrap print file 1640 that is generated by the processor(s) 1710. The 3D printer 1760 may be coupled to the processor(s) 1710 via the interconnect 1730. In some embodiments, the 3D printer 1760 may be coupled to the processor(s) 1710 via the communication adapter(s) 1740.

As will be appreciated by one skilled in the art, aspects of the embodiments taught herein may be illustrated and described herein in any of a number of patentable classes or context including any new and useful process, machine, manufacture, or composition of matter, or any new and useful improvement thereof. Accordingly, aspects of the embodiments taught herein may be implemented by entirely hardware, entirely software (including firmware, resident software, micro-code, etc.) or combining software and hardware implementation that may all generally be referred to herein as a "circuit," "module," "component," or "system." Furthermore, aspects of the embodiments taught herein may take the form of a computer program product embodied in one or more computer readable media having computer readable program code embodied thereon.

Any combination of one or more computer readable media may be utilized. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. As used herein, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the embodiments taught herein may be written in any combination of one or more programming languages, including an object oriented programming language such as Java, Scala, Smalltalk, Eiffel, JADE, Emerald, C++, C #, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the embodiments are described herein with reference to flowchart illustrations and/or block diagrams of methods, apparatus (systems) and computer program products according to embodiments taught herein. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The embodiments taught herein are explained in greater detail in the following non-limiting examples.

EXAMPLES

This example describes the design, formation, and use of a ventricular support device as taught herein. Left ventricular remodeling secondary to dilated cardiomyopathy is a cause for various cardiac complications in patients that affect their quality of life and may even be life-threatening. Previous support devices designed to attenuate the progression of the condition showed mixed results and are still in active progress towards developing better devices. Unlike others, the embodiments taught herein focus on developing a structural framework that could be parametric based on the patient's imaging data and printing the device using a 3D printer, to provide a customized device.

Materials and Methods

Digital Imaging and Communications in Medicine (DICOM) images of a patient with dilated cardiomyopathy were retrieved. The data consisted of several views of the patient's heart obtained using a computed tomography (CT) scanner. A 3D workstation (Osirix 3.6.1, Geneva, Switzerland) was used to make 6 measurements of the heart's dimension at end-diastole at two different views of the heart. Then, a third party software (Rhinoceros OSX, Seattle, WA.) was used to design a 3D ventricular wrap using the measurements to compose interpolated curve sections which served as the base for a network surface.

PLCL was selected as a biodegradable material for the 3D ventricular wrap. PLCL compositions of 50:50, 70:30, 75:25, and 80:20 were investigated. A ratio of 70:30 was selected as it provided the correct elasticity and stress for the patient. The stress generated by the wrap once it has expanded a given distance (which is determined by using DICOM images to calculate how much the patient's heart expanded between systole and diastole) was selected to match an amount of stress calculated using the stress/strain curve for the patient.

Figure 18A:
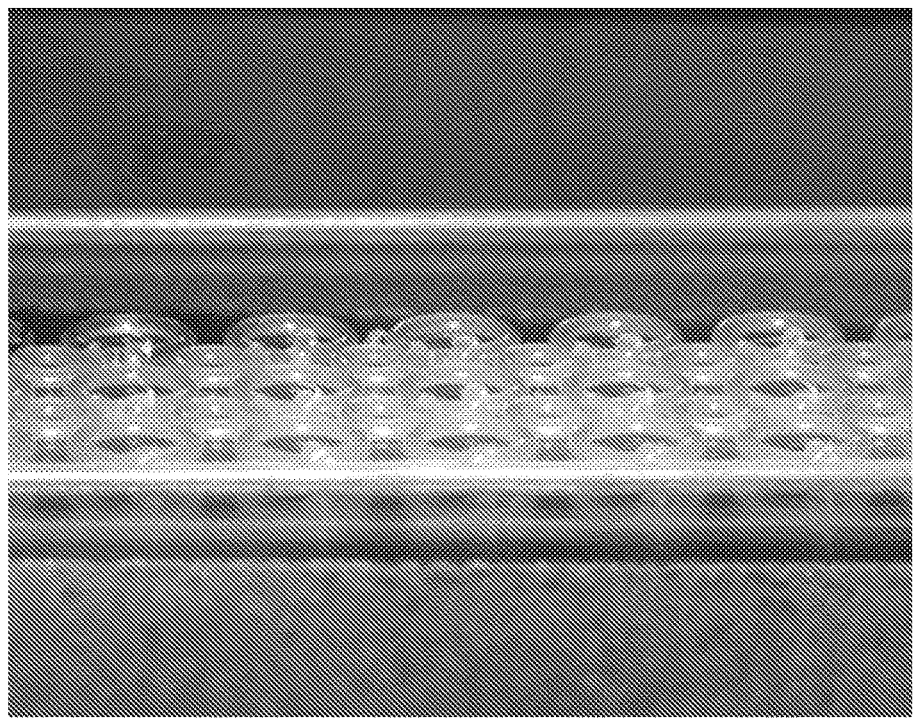
FIGS. 18A-B are photographs of example sheet designs for a ventricular support device formed using a 3D printer.
Figure 18B:
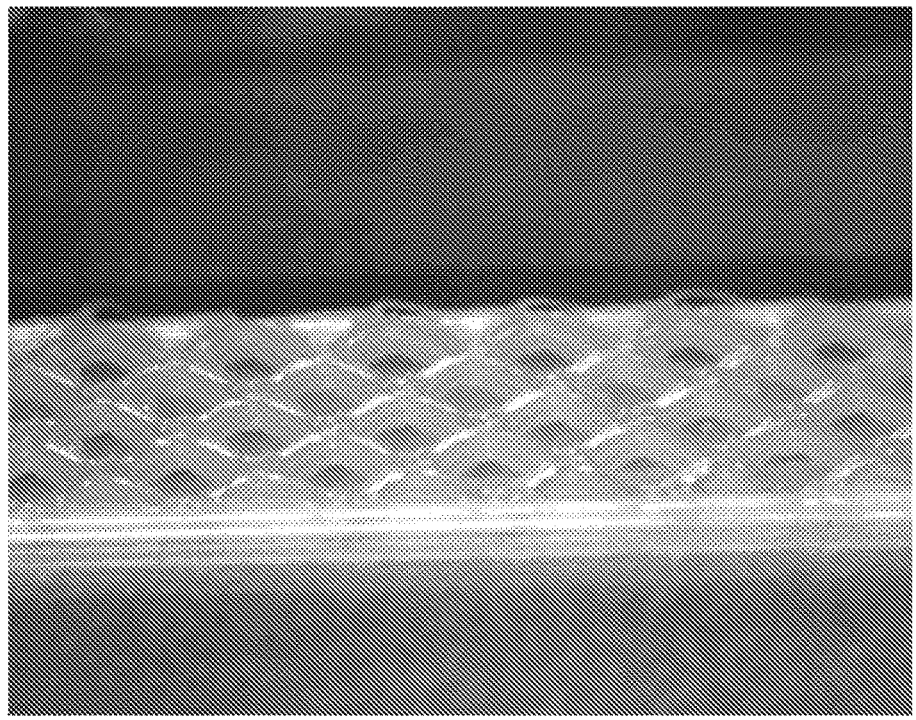

Different types of mesh designs were investigated for the mesh of the 3D ventricular wrap, including the use of interconnected circles, ellipses, and diamonds. A diamond mesh structure was ultimately selected. FIGS. 18A and 18B show mesh sheet designs printed using biodegradable materials using circles and diamonds, respectively. After trying different shapes, the diamond mesh shape was selected because it allowed the wrap to stretch the most without compromising the integrity of the device.

In addition, various aspects of the 3D ventricular wrap were investigated, including the beam width and extrusion height of the printed model, as well as the height of the diamond structure used in the mesh. The beam width was selected to be 0.6 mm, and the extrusion height was selected to be 0.6 mm. The diamond shape within the mesh was selected to have a height of 10 mm with an internal angle of 160 degrees.

Both vertical and horizontal printing were explored with respect to forming the 3D ventricular wrap. Ultimately, horizontal printing was selected. Once printed, the 3D ventricular wrap had a polygon shape similar to that of FIG. 11A, with an upper width of 12.1 cm, a lower width of 9 cm and a height of 6 cm. When opposing edges of the 3D ventricular wrap were connected to one another, the 3D ventricular wrap formed a conical frustum whose largest diameter was 3.6 cm.

Results

Figure 19:
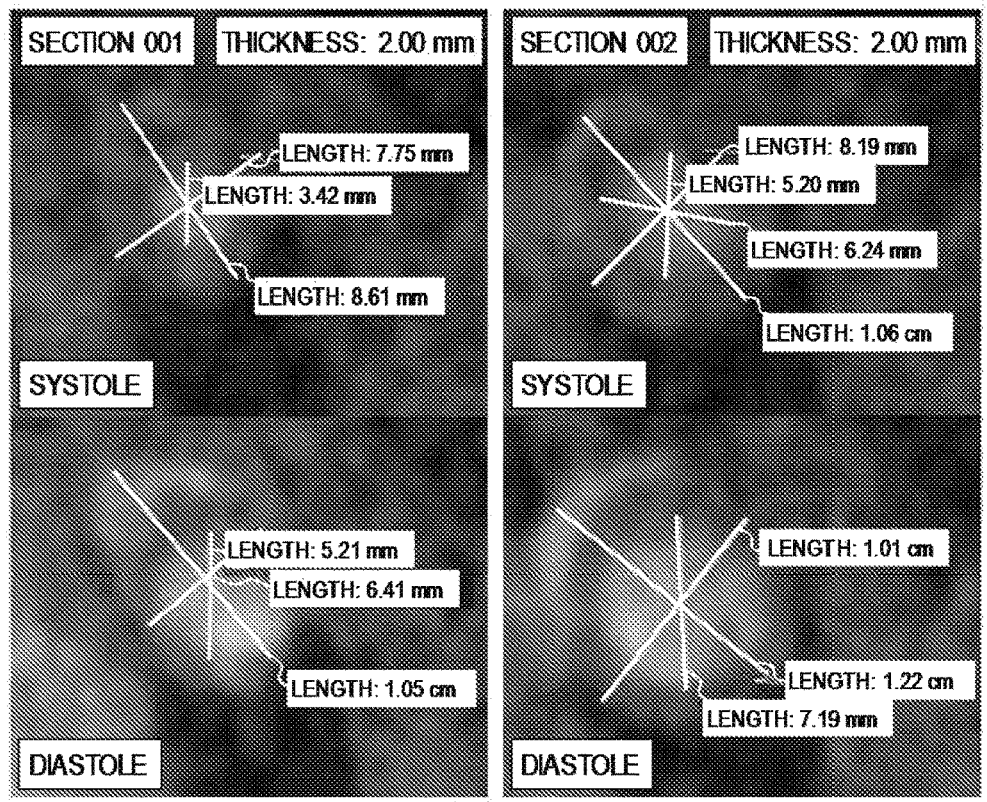
FIG. 19 shows examples scans of a rat heart that may be used to develop a 3D heart model according to some embodiments taught herein.
Figure 19:
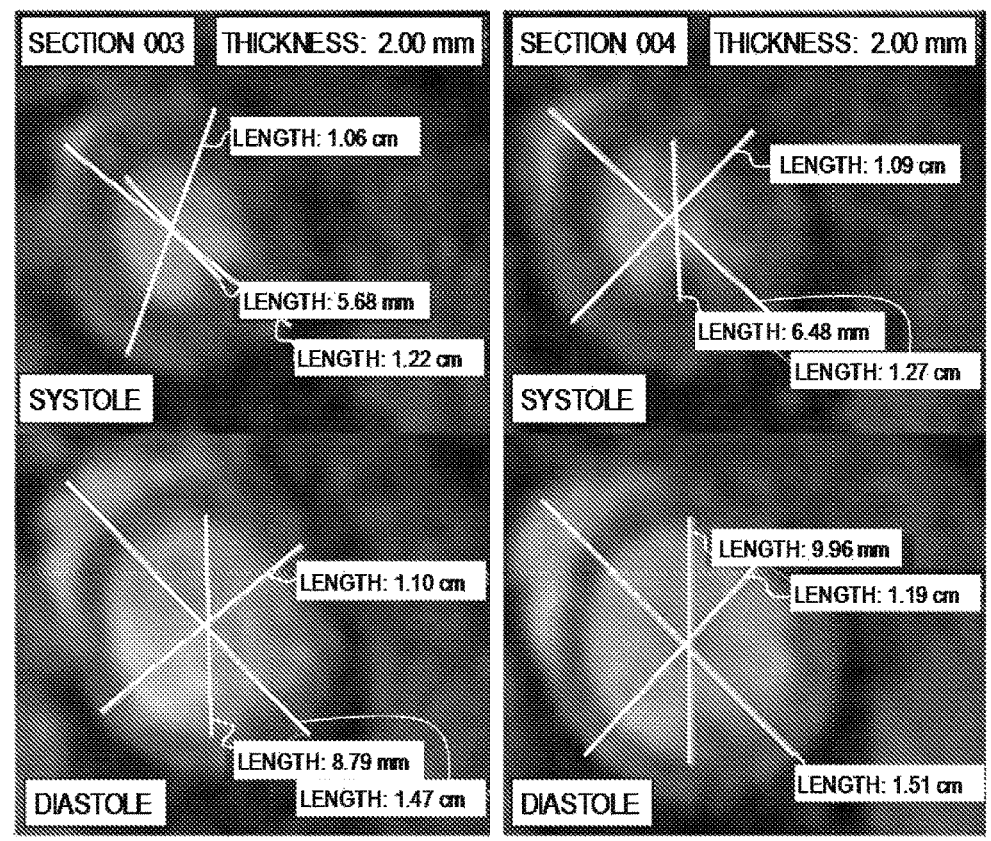

Using DICOM images with a combined utilization of a DICOM viewer and software employed by architects and structural engineers, a 3D model representing a ventricular support device that tailors around the patient's heart was developed. The modelling process was executed for a rat heart to provide a printed ventricular support device. As illustrated in FIG. 19, the rat's heart was first scanned using a DICOM imaging viewer. OSIRIX MD, developed by Pixmeo SARL, of Geneva, Switzerland, was used to take measurements of the rat's heart in both systole and diastole at slices 2 mm apart along the long-axis. Each slice was offset at 2 mm apart, however, other slice spacings are possible.

Figure 20:
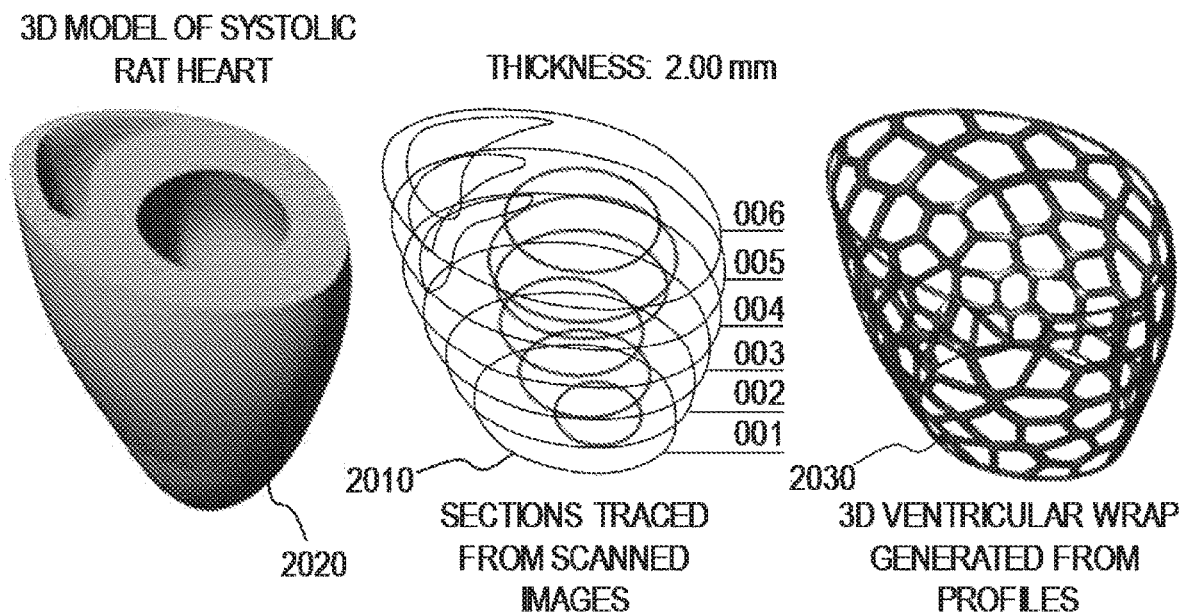
FIG. 20 illustrates an example of forming a model for a ventricular support device using the 3D heart model of FIG. 19.
Figure 21:
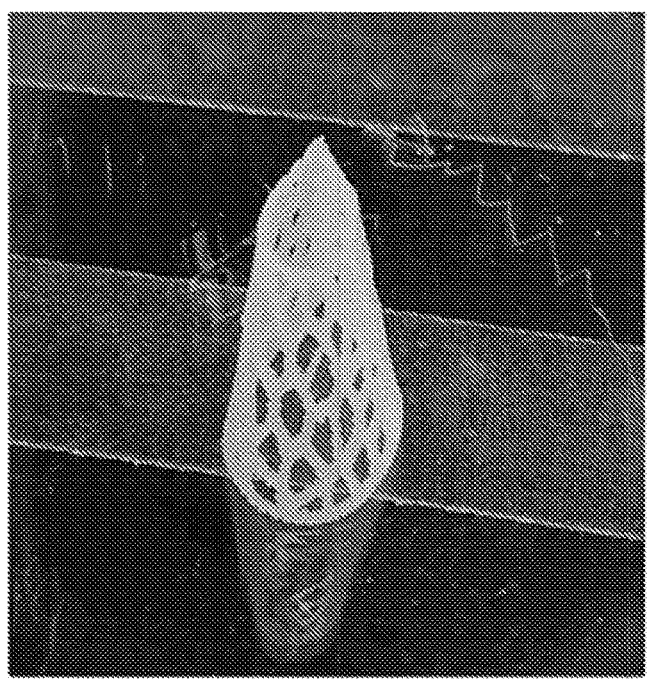
FIG. 21 shows a 3D printed ventricular support device printed using the model for the ventricular support device of FIG. 20.

Based on the measurements provided by the imaging data, a 3D visualization was generated using GRASSHOPPER 3D and RHINOCEROS 3D modelling tools. RHINOCEROS 3D is a commercial 3D software package produced by Robert McNeel & Associates of Seattle, WA. GRASSHOPPER 3D, also from Robert McNeel & Associates, is a visual programming language that integrates with RHINOCEROS 3D. As illustrated in FIG. 20, the scans provided physical dimensions of the rat heart 2010 that could then be used to form a 3D model of the rat heart 2020. Based on the 3D model of the rat heart 2020, the surfaces of the 3D model of the rat heart 2020 were analyzed and the topology of a mesh support covering said surfaces was developed. As illustrated in FIG. 20, the mesh for the model of the ventricular support device used a Voronoi pattern. Using the 3d model of the rat heart 2020, a design for the ventricular support device 2030 for the rat's heart was developed that was configured to surround and support the surfaces of the rat's heart. FIG. 21 illustrates a 3D printed ventricular support device 2100 printed using the design for the ventricular support device 2030.

The 3D model representing the ventricular support device may be additionally customized using strain data that can be generated for the patient's heart. The strain data identifies the strain for various areas of the patient's heart and provides an indication of elements of the 3D model representing the ventricular support device which require greater or lesser support.

Synthesis of Alternative Materials for the 3D Ventricular Wrap

Figure 22A:
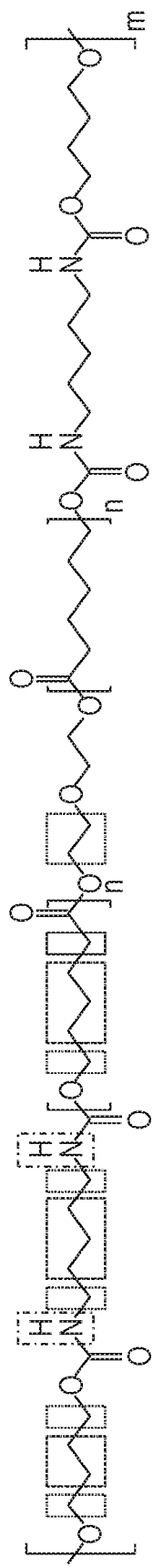
FIG. 22A shows the structure of a biodegradable thermoplastic polyurethane (TPU) elastomer with linear crosslinking that was synthesized from hexamethylene diisocyanate, polycaprolactone (PCL) diol, and 1,4-Butanediol.
Figure 22B:
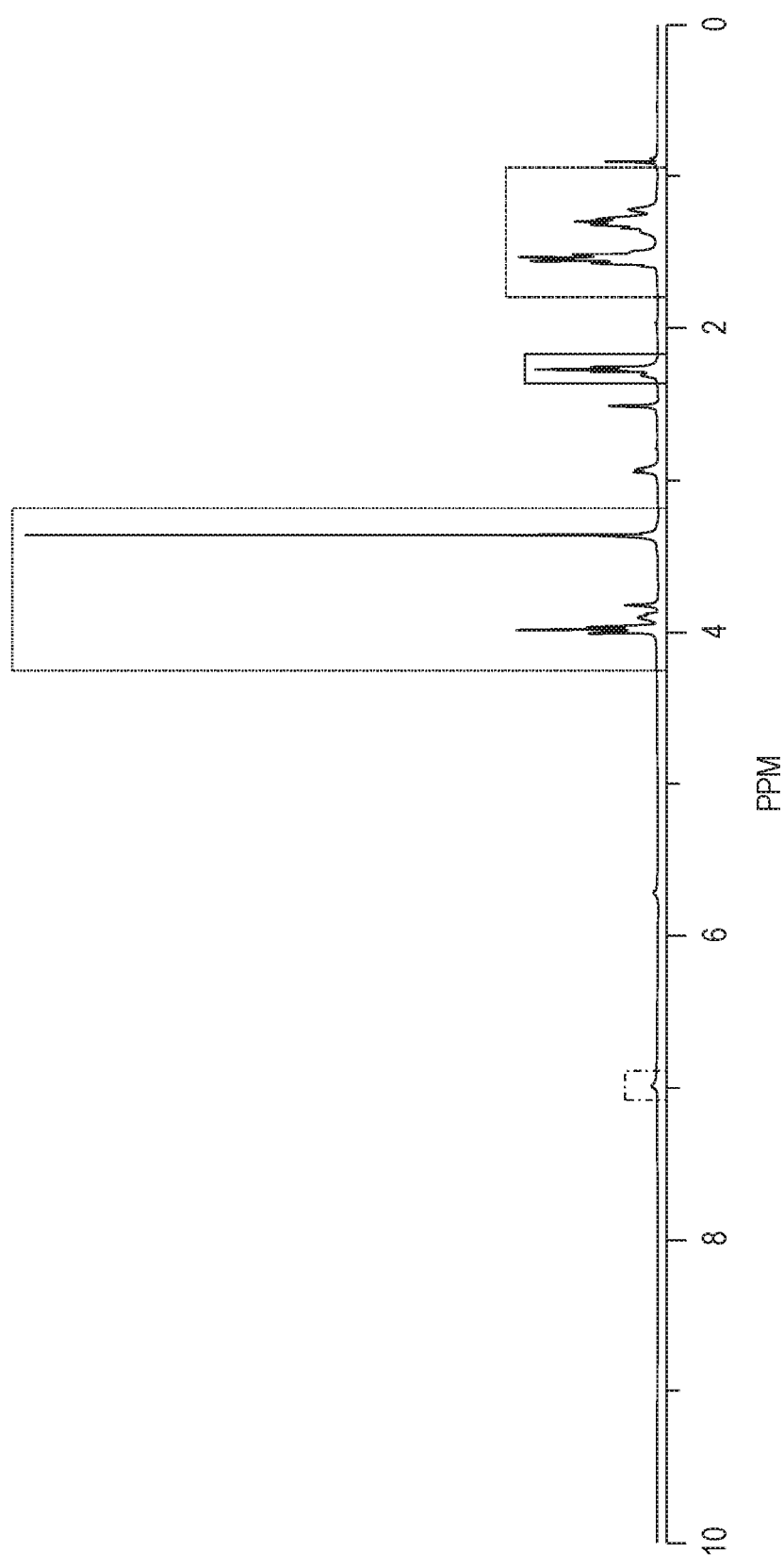
FIG. 22B presents the NMR spectrum verifying the chemical structure of the formed polymer shown in FIG. 22A.

A biodegradable thermoplastic polyurethane (TPU) elastomer with linear crosslinking was synthesized from hexamethylene diisocyanate, polycaprolactone (PCL) diol, and 1,4-Butanediol. The NMR spectrum verified the chemical structure of the polymer and suggested that the intended TPU was successfully synthesized (FIGS. 22A and 22B).

The foregoing is illustrative of the present invention, and is not to be construed as limiting thereof. The invention is defined by the following claims, with equivalents of the claims to be included therein.

That which is claimed is:

1. A method of forming a ventricular support device for a diseased heart, comprising:
   providing imaging data of the diseased heart;
   forming a three-dimensional (3D) heart model based on the imaging data;
   providing strain data, said strain data comprising a plurality of strain estimates each corresponding to a respective segment of the diseased heart;

mapping the plurality of strain estimates onto corresponding portions of the 3D heart model to form a 3D diseased heart model;
based on the 3D diseased heart model, forming a model of the ventricular support device, said ventricular support device configured to surround at least a portion of the diseased heart and provide different support to the segments of the diseased heart based upon said strain estimates;
converting the model of the ventricular support device to a digital file, said digital file configured to direct a 3D printer device to print said ventricular support device for said diseased heart; and
printing the ventricular support device with the 3D printer device, resulting in the ventricular support device.

2. The method of claim 1, wherein said forming the 3D heart model comprises making multiple measurements of dimensions of the diseased heart and using said measurements to form the 3D heart model.

3. The method of claim 1, wherein said forming the model of the ventricular support device comprises:
associating a first segment of the 3D diseased heart model with a first mapping between a first strain estimate of the plurality of strain estimates and a first portion of the 3D heart model;
associating a second segment of the 3D diseased heart model with a second mapping between a second strain estimate of the plurality of strain estimates and a second portion of the 3D heart model; and
forming the model of the ventricular support device such that greater reinforcement is provided to the first segment of the 3D diseased heart model than the second segment of the 3D diseased heart model when it is determined that the first strain estimate is greater than the second strain estimate.

4. The method of claim 1, wherein said printing is carried out using a biodegradable material to form a ventricular support device that is biodegradable.

5. The method of claim 4, wherein the biodegradable material comprises poly(L-lactide-co-caprolactone) (PLCL).

6. The method of claim 4, wherein the biodegradable material comprises an elastomeric polyester.

7. The method of claim 1, wherein the ventricular support device comprises a mesh structure.

8. The method of claim 1, further comprising:
providing an index structure on the ventricular support device.

9. The method of claim 8, wherein the index structure comprises a first color different from a second color of material surrounding the index structure.

10. A method of treating ventricular remodeling in a heart of a subject in need thereof, comprising:
providing imaging data of the heart;
forming a three-dimensional (3D) heart model based on the imaging data of the heart;
providing strain data comprising a plurality of strain estimates each corresponding to a respective segment of the heart;
mapping the plurality of strain estimates onto corresponding portions of the 3D heart model to form a 3D diseased heart model;
based on the 3D diseased heart model, forming a model of a ventricular support device, said ventricular support device configured to surround at least a portion of the heart and provide different support to the segments of the diseased heart based upon said strain estimates;
converting the model of the ventricular support device to a digital file, said digital file configured to direct a 3D printer device to print said ventricular support device;
printing said ventricular support device by said 3D printer device and using said digital file; and
administering said ventricular support device to the heart of said subject.

11. The method of claim 10, wherein said ventricular remodeling is left ventricular remodeling.

12. The method of claim 10, wherein said subject has dilated cardiomyopathy.

13. The method of claim 10, wherein said subject has congested heart failure.

14. The method of claim 10, wherein said subject has suffered from myocardial infarction.

15. The method of claim 10, wherein said subject is a human subject.

16. The method of claim 10, wherein said ventricular support device is biodegradable.

17. The method of claim 10, wherein said administering is carried out by laparoscopic surgery.

18. A computer system comprising:
a processor; and
a three-dimensional (3D) printer device communicatively coupled to the processor;
a memory coupled to the processor and comprising computer readable program code that when executed by the processor causes the processor to perform operations comprising:
receiving imaging data of a diseased heart;
forming a 3D heart model based on the imaging data;
receiving strain data, said strain data comprising a plurality of strain estimates each corresponding to a respective segment of the diseased heart;
mapping the plurality of strain estimates onto corresponding portions of the 3D heart model to form a 3D diseased heart model;
based on the 3D diseased heart model, forming a model of a ventricular support device, said ventricular support device configured to surround at least a portion of the heart and provide different support to the segments of the diseased heart based upon said strain estimates; and
converting the model of the ventricular support device to a digital file, said digital file configured to direct the 3D printer device to print said ventricular support device for said diseased heart; and
printing, using the digital file, the ventricular support device with the 3D printer device.

19. The computer system of claim 18, wherein said forming the 3D heart model comprises making multiple measurements of dimensions of the diseased heart and using said measurements to form the 3D heart model.

20. The computer system of claim 18, wherein said forming the model of the ventricular support device comprises:
associating a first segment of the 3D diseased heart model with a first mapping between a first strain estimate of the plurality of strain estimates and a first portion of the 3D heart model;
associating a second segment of the 3D diseased heart model with a second mapping between a second strain estimate of the plurality of strain estimates and a second portion of the 3D heart model; and
providing greater reinforcement to the first segment of the 3D diseased heart model than the second segment of the 3D diseased heart model when it is determined that the first strain estimate is greater than the second strain estimate.

21. The computer system of claim 18, wherein the processor further performs operations comprising:
providing an index structure on the ventricular support device printed by the 3D printer.

22. A computer program product comprising:
a tangible non-transitory computer readable storage medium comprising computer readable program code embodied in the computer readable storage medium that when executed by at least one processor causes the at least one processor to perform operations comprising:
receiving imaging data of a diseased heart;
forming a three-dimensional (3D) heart model based on the imaging data;
receiving strain data, said strain data comprising a plurality of strain estimates for each corresponding to a respective segment of the diseased heart;
mapping the plurality of strain estimates onto corresponding portions of the 3D heart model to form a 3D diseased heart model;
based on the 3D diseased heart model, forming a model of a ventricular support device, said ventricular support device configured to surround at least a portion of the heart and provide support based upon said strain estimates;
converting the model of the ventricular support device to a digital file, said digital file configured to direct printing of said ventricular support device for said diseased heart; and
printing the ventricular support device with a 3D printer device connected to the processor using the digital file.

23. The computer program product of claim 22, wherein said forming the 3D heart model comprises making multiple measurements of dimensions of the diseased heart and using said measurements to form the 3D heart model.

24. The computer program product of claim 22, wherein said forming the model of the ventricular support device comprises:
associating a first segment of the 3D diseased heart model with a first mapping between a first strain estimate of the plurality of strain estimates and a first portion of the 3D heart model;
associating a second segment of the 3D diseased heart model with a second mapping between a second strain estimate of the plurality of strain estimates and a second portion of the 3D heart model; and
providing greater reinforcement to the first segment of the 3D diseased heart model than the second segment of the 3D diseased heart model when it is determined that the first strain estimate is greater than the second strain estimate.

25. The computer program product of claim 22, wherein the computer readable program code causes the processor to further perform operations comprising:
providing an index structure on the ventricular support device printed by the 3D printer.

26. A customized ventricular support device for a diseased heart, comprising:
a mesh structure configured to enclose at least a portion of the diseased heart,
wherein a first portion of the mesh structure is configured to contact and support a first portion of the diseased heart,
wherein a second portion of the mesh structure is configured to contact and support a second portion of the diseased heart,
wherein a first characteristic of the first portion of the mesh structure is different than a second characteristic of the second portion of the mesh structure responsive to differences in strain estimates between the first and second portions of the diseased heart.

27. The customized ventricular support device of claim 26, wherein the mesh structure comprises a biodegradable material.

28. The customized ventricular support device of claim 27, wherein the biodegradable material comprises an elastomeric polyester, and optionally wherein the elastomeric polyester is crosslinked.

29. The customized ventricular support device of claim 26, wherein the mesh structure comprises a diamond lattice or a Voronoi pattern.

30. The customized ventricular support device of claim 26, further comprising:
an index structure on the ventricular support device.

31. The customized ventricular support device of claim 30, wherein the index structure comprises a first color different from a second color of material surrounding the index structure.

32. The customized ventricular support device of claim 27, wherein the biodegradable material comprises poly(L-lactide-co-caprolactone) (PLCL).

33. The customized ventricular support device of claim 26, wherein the mesh structure is produced by a 3D printer.

34. The method of claim 6, wherein the elastomeric polyester is crosslinked.

* * * * *

UNITED STATES PATENT AND TRADEMARK OFFICE
CERTIFICATE OF CORRECTION

PATENT NO. : 11,779,464 B2  
APPLICATION NO. : 16/618926  
DATED : October 10, 2023  
INVENTOR(S) : Kim et al.

Page 1 of 1

It is certified that error appears in the above-identified patent and that said Letters Patent is hereby corrected as shown below:

In the Specification

Column 25, Line 19: Please correct "plurality of strain estimates for each corresponding" to read --plurality of strain estimates each corresponding--

Signed and Sealed this
Twenty-sixth Day of December, 2023

Katherine Kelly Vidal
*Director of the United States Patent and Trademark Office*